United States Patent
Pendleton et al.

(10) Patent No.: US 11,612,501 B2
(45) Date of Patent: Mar. 28, 2023

(54) HIP AND KNEE JOINT STEM EXPLANT SYSTEM AND METHODS OF USING THE SAME

(71) Applicants: John E. Pendleton, Atlanta, GA (US); Daniel H. Hursh, Roswell, GA (US); Mary Katlyn Pitz, Atlanta, GA (US); Benjamin McKee Stronach, Madison, MS (US)

(72) Inventors: John E. Pendleton, Atlanta, GA (US); Daniel H. Hursh, Roswell, GA (US); Mary Katlyn Pitz, Atlanta, GA (US); Benjamin McKee Stronach, Madison, MS (US)

(73) Assignee: Tightline Development, LLC., Atlanta, GA (US)

( * ) Notice: Subject to any disclaimer, the term of this patent is extended or adjusted under 35 U.S.C. 154(b) by 766 days.

(21) Appl. No.: 16/657,581

(22) Filed: Oct. 18, 2019

(65) Prior Publication Data
US 2020/0121474 A1    Apr. 23, 2020

Related U.S. Application Data

(60) Provisional application No. 62/747,778, filed on Oct. 19, 2018.

(51) Int. Cl.
*A61F 2/46* (2006.01)

(52) U.S. Cl.
CPC ............ *A61F 2/4607* (2013.01); *A61F 2/461* (2013.01); *A61F 2/4609* (2013.01); *A61F 2/4603* (2013.01); *A61F 2002/4619* (2013.01); *A61F 2002/4622* (2013.01); *A61F 2002/4681* (2013.01)

(58) Field of Classification Search
CPC ...... A61F 2/4607; A61F 2/4609; A61F 2/461; A61F 2/4603; A61F 2002/4619; A61F 2002/4622; A61F 2002/4681
USPC ......................................... 606/84, 79–81, 91
See application file for complete search history.

(56) References Cited

U.S. PATENT DOCUMENTS

| | | | |
|---|---|---|---|
| 4,896,663 A | 1/1990 | Vandewalls | |
| 5,830,215 A | 11/1998 | Incavo et al. | |
| 6,063,124 A | 5/2000 | Amstutz | |
| 6,152,930 A | 11/2000 | Mastrorio | |
| 6,565,575 B2 | 5/2003 | Lewis | |
| 7,344,565 B2 | 3/2008 | Seyer et al. | |
| 7,744,602 B2 * | 6/2010 | Teeny | A61F 2/4609 606/100 |
| 7,763,031 B2 | 7/2010 | Tulkis | |
| 7,879,042 B2 | 2/2011 | Long | |
| 7,942,883 B2 | 5/2011 | Teeny et al. | |
| 7,998,146 B2 | 8/2011 | Anderson | |
| 8,034,059 B2 | 10/2011 | Tulkis | |
| 8,282,649 B2 | 10/2012 | Long et al. | |
| 8,475,465 B2 | 7/2013 | Teeny et al. | |

(Continued)

OTHER PUBLICATIONS

Biomet, "Vanguard™ Lock-on Femoral Impactor—Instructions for Proper Use and Inspection Technique", 2008, 5 pages.

(Continued)

*Primary Examiner* — Jessica Weiss
(74) *Attorney, Agent, or Firm* — FisherBroyles, LLP; Anthony Dovale; John Boyd

(57) ABSTRACT

Systems, instruments, tools and methods for facilitating the removal of a knee or hip implants and other bone implants.

21 Claims, 15 Drawing Sheets

(56) References Cited

U.S. PATENT DOCUMENTS

| | | | |
|---|---|---|---|
| 8,801,724 B2 | 8/2014 | Zumsteg et al. | |
| 8,834,478 B2 | 9/2014 | Turner et al. | |
| 8,834,480 B2 * | 9/2014 | Hudak, Jr. | A61F 2/4609 606/86 R |
| 8,888,783 B2 | 11/2014 | Young | |
| 9,089,440 B2 | 7/2015 | Mueller | |
| 9,289,218 B2 | 3/2016 | Courtney, Jr. et al. | |
| 9,724,209 B2 | 8/2017 | Kim | |
| 9,763,673 B2 | 9/2017 | Young | |
| 9,763,676 B2 | 9/2017 | Motherway et al. | |
| 9,770,279 B2 | 9/2017 | Kellar et al. | |
| 9,931,225 B2 * | 4/2018 | Hudak, Jr. | A61F 2/4609 |
| 10,463,507 B2 * | 11/2019 | Nic | A61B 17/1666 |
| 10,905,564 B2 * | 2/2021 | Slater | A61F 2/4609 |
| 2002/0116007 A1 * | 8/2002 | Lewis | A61F 2/4609 606/99 |
| 2006/0195105 A1 * | 8/2006 | Teeny | A61F 2/4609 606/76 |
| 2006/0200165 A1 * | 9/2006 | Tulkis | A61B 17/1666 606/99 |
| 2015/0119891 A1 * | 4/2015 | Goldberg | A61B 17/1631 606/80 |
| 2015/0359641 A1 | 12/2015 | Nic | |
| 2016/0100957 A1 | 4/2016 | Lewis | |
| 2016/0157911 A1 | 6/2016 | Courtney, Jr. et al. | |
| 2016/0206326 A1 | 7/2016 | Gilhooley | |
| 2017/0202681 A1 | 7/2017 | Giardiello et al. | |

OTHER PUBLICATIONS

Depuy Synthes, "Hip Extraction Instrument", Product Overview, Revision Solutions, 2014, 16 pages.
Stryker, "EZout System components", Technique Guide, 2016, 2 pages.
Zimmer, "Explant® Acetabular Cup Removal System Surgical Technique", 2011, 12 pages.
Innomed, "CupX—acetabular cup extraction system", Jan. 2012, 6 pages.
Innomed, "Femoral Component Extractor", 2012, 1 page.
Innomed, "Flexible Osteotome System", 2015, 1 page.
Innomed, "Modified Lambotte Cup Removal Osteotomes", 2010, 1 page.
Innomed, "Modified Smith Petersen Style Osteotomes for Acetabular Cup Removal", 2006, 1 page.
Innomed, "Mueller-Type Cement Removal Instruments", 2015, 1 page.
Innomed, "Universal Hip Cup Removal System", as accessed on Oct. 22, 2019, 4 pages.
Innomed, "Whelan Curved Chisel Guide", 2016, 1 page.
Innomed, "Whelan Flexible Chisel Guide", 2014, 1 page.
Shukla Medical, "Xtract-All-Hip—Universal Hip Stem Extraction System", as accessed on Oct. 22, 2019, 2 pages.
Shukla Medical, "Xtract-All-Knee—Universal Knee Implant Extraction System", Surgical Technique Guide, as accessed on Oct. 22, 2019, 11 pages.
Shukla Medical, "Modular Hip Stem Extractor", Surgical Technical Guide, as accessed on Oct. 22, 2019, 3 pages.

* cited by examiner

HIP AND KNEE JOINT STEM EXPLANT SYSTEM AND METHODS OF USING THE SAME

RELATED APPLICATIONS

This application claims the benefit of and priority to U.S. Provisional Application No. 62/747,778, filed Oct. 19, 2018 entitled "Hip and Knee Stem Explant System and Methods of Using the Same", which is hereby incorporated by reference in its entirety.

FIELD OF THE INVENTION

The present invention relates generally to systems, instruments, components, and methods for the removal of hip, knee and other bone-related implants. More specifically, the present invention relates to a system comprising handles and attachments that facilitate the removal of a prosthetic implant from the femur, tibia, acetabulum and other bone(s), and methods of using the same.

BACKGROUND OF THE INVENTION

Conventional, primary total hip and knee replacement is a proven operation that results in improved hip mobility and function in the majority of patients. A total hip replacement implant is a mechanical device comprised of two parts: a ball and a socket. A total knee replacement implant is a mechanical device comprised of two parts: femoral condyle(s) and a tibial plateau platform. As with any other mechanical implant, a total joint replacement is subject to various forms of mechanical wear and biological conditions which can result in mechanical or biological failure. Such a failure may require a reoperation of the joint replacement to address the cause of failure and its consequences. A reoperation of a total joint replacement is called a revision.

The parts of a joint replacement which move against one another will slowly wear down during the regular use of the replacement. The more physically active the patient is, the faster the wear. Continual, repetitive movement of the mechanical parts can cause degradation in which small pieces of hip and knee prosthesis "shed" or flake off. Depending on the type of joint replacement, these particles can be made out of plastic, cement, ceramic, or metal.

Mechanical wear and tear leading to loosening of the prosthesis (implant) is one of the most common forms of mechanical failure. Other forms of mechanical failure are possible, however, and can include breakage of the prosthesis during a trauma like a fall or auto collision.

When a patient experiences failure of their implant and/or other issue with the implant (e.g., adverse reaction), a surgeon will often perform revision surgery. During the revision, the failed components of the existing implant are removed and replaced. Due to the dynamic nature of the biologic environment, total hip and knee implants are subject to bony ingrowth, such that it can be difficult to remove an implant requiring revision. Accordingly, it is desirable to provide a system that can assist the surgeon in removing the implant in an efficient manner with the least amount of damage to the bone and surrounding tissue.

SUMMARY

The invention relates to systems for the removal of hip and knee implants and other implants, along with the appropriate methods of using the same for extracting such implants.

More specifically, the invention relates to Femoral Hip Stem, Acetabular Cup, Femoral Knee, and Tibial Knee Explant systems that facilitate the removal of prosthetic implants from the femur, tibia, acetabulum and other bone or bone structures, and methods of using the same.

According to preferred embodiments, the systems include modular handles have a standard Hudson connection or other quick connect adaptor for use with various attachments, preferably interchangeable attachments adapted for different purposes, implant sizes and/or configurations. Advantageously, the use of instruments having modular components allow the instrument to be modified and customized to optimize the instrument for the user and the size, configuration and location of the implant to be extracted. The attachments include instruments, devices or tools that interface with implants for extracting or for the breakup of bone cement/bone ingrowth at the implant interface with bone to facilitate removal. The handles, preferably modular, are configured to directly apply impact force, extraction force, and torque depending on the surgical approach angle, the instrument being employed, and the implant being removed. The slap hammer, for example, is used to apply extreme extraction force. Preferably, the attachments allow connection to the handle or hammer using Hudson adaptors (herein called "Hudson attachments" which includes other quick connect attachments) and include threaded assemblies for direct implant connection and removal.

One aspect of the invention relates to a system for removing a hip stem and acetabular cup implant from a femur comprising:
  (a) at least two modular handles and at least one modular slap hammer, and
  (b) at least five, preferably at least ten, modular blades and/or at least two modular tools configured for facilitating the removal of the implant,
  wherein each modular blade and/or modular tool includes a proximal end configured to be attached to at least one modular handle or at least one modular slap hammer and a distal end including a cutting tip configured to cut through and/or remove bone growth into the implant thereby facilitating removal of the implant.

Another aspect of the invention relates to a system for removal of a tibial plate and femoral knee implant comprising:
  (a) at least one modular handle and at least one modular slap hammer, and
  (b) at least three modular blades and/or at least three modular tools configured for facilitating the removal of the implant,
  wherein each modular blade and/or modular tool includes a proximal end configured to be attached to at least one modular handle and/or at least one modular slap hammer and wherein a distal end of the modular blade or modular tool includes a cutting tip configured to cut through and/or remove bone growth into the implant thereby facilitating removal of the implant.

Another aspect of the invention relates to a modular tool for removing a femoral stem implant comprising:
  (a) a modular handle configured for mallet impaction,
  (b) at least one modular adaptor attached to the modular handle and configured to connect other modular components to the modular handle, and
  (c) a modular component attached to the modular handle via the adaptor and configured for cutting bone and/or removing the implant;
    wherein the modular tool is configured for mallet impaction and extraction while maintaining connection to the modular handle and controlling the position of the modular component to break bone ingrowth away from the femoral stem implant.

Preferably, the modular component is an osteotome.

Preferably, the at least one modular adaptor is a Hudson adaptor or other quick connect adaptor.

Another aspect of the invention relates to a modular tool for removing an implant comprising:
(a) a modular handle, wherein the modular handle includes a threaded adaptor having at least one joint configured to connect to at least one modular component, and
(b) a modular extraction tool connected to the at least one joint;
wherein the extraction tool is configured to break bone ingrowth away from the implant and the at least one joint is configured to allow the modular extraction tool to maneuver relative to the modular handle.

Another aspect of the invention relates to a modular tool for removing an implant comprising:
(a) a modular slap hammer mass, wherein the modular slap hammer mass has an inner channel from a first end to a second end of the modular slap hammer mass, and
(b) a shaft passing through the inner channel, wherein the shaft has a first end configured to attach to an implant removal tool and the modular slap hammer mass is configured to slide along the modular shaft to create an impaction force to assist the implant removal tool remove the implant and/or remove cement/bone adjacent the implant.

According to preferred embodiments, the shaft is an elongated shaft.

According to alternative embodiments, the shaft is an extendible shaft, preferably a telescoping shaft.

Another aspect of the invention relates to an instrument for removal of an acetabular cup comprising:
(a) an elongated handle;
(b) an acetabular cup removal assembly attached to the elongated handle,
wherein the acetabular cup removal assembly includes: (i) an interchangeable head for positioning and stabilizing the instrument within an acetabular liner or shell and (ii) an adjustable curved blade positioned to track around the outer diameter of the acetabular liner or shell to break the bone in-growth and/or adjacent bone.

Another aspect of the invention relates to an instrument for removal of an implant, the instrument comprising:
(a) a modular handle; and
(b) a modular ball nose driver having hexalobe screws adapted to adjust at variable angles allowing for engagement of the modular ball nose driver and configured to connect to a modular surgical tool.

Another aspect of the invention relates to an instrument for removal of a knee femoral component comprising:
(a) a handle having a strike plate at a first end and a second end including a connector;
(b) a femoral knee remover assembly configured to connect to the handle via the connector, wherein the modular femoral knee remover assembly comprises an adjustable arm blade configured to accommodate variable widths of implants.

Another aspect of the invention relates to a modular femoral knee remover comprising a connecting shaft having a threaded adaptor configured to allow the modular femoral knee remover assembly to connect to a slap hammer.

Another aspect of the invention relates to an instrument comprising a tibial knee plate remover assembly, wherein the tibial knee plate remover assembly comprises at least one adjustable arm blade adapted to clear a tibial implant and compress under the implant to break the bone/bone cement interface.

Another aspect of the invention relates to a slap hammer assembly for implant extraction comprising:
a) a slap hammer mass having a central channel;
b) a shaft passing through the central channel;
c) a T-handle connected to the shaft configured to allow the user to stabilize the shaft of the slap hammer during implant extraction;
d) a modular U-joint connected to the slap hammer; and
e) a modular extension grip connected to the U-joint;
wherein the U-Joint connects to (preferably threads into) the slap hammer mass on one side and connects to (preferably is threaded to) the extension grip on the other side. According to an alternative embodiment, the U-Joint connects to (preferably threads into) the shaft (and not the hammer mass).

Another aspect of the invention relates to a femoral stem threaded adaptor comprising a first end having a first set of threads adapted to engage with corresponding threads on an implanted femoral stem and a second end having a second set of threads configured to allow the adaptor to engage a tool (e.g., slap hammer instrument) for extraction of the implant.

Another aspect of the invention relates to a stem yoke attachment having a first end comprising a hoop configured to contour to a stem taper to lock onto the stem neck and a second end adapted to attach to a slap hammer having a shaft.

Another aspect of the invention relates to a stem grabber having a first end comprising an adjustable hoop configured to contour to a stem taper to adjust and lock onto the stem neck and a second end adapted to attach to a slap hammer having a shaft.

Another aspect of the invention relates to a cement drill system for drilling through bone cement within a canal within a bone (e.g., a femur), the cement drill system comprising:
(a) an elongated cement drill having a proximal end including an adaptor for connecting the cement drill to a handle, drilling device or other component and a distal end comprising a distal lip on a side of the elongated cement drill; and
(b) at least one cylindrical centralizer having a central channel for the elongated cement drill to pass therethrough and a side opening along the length of the centralizer and configured to allow the distil lip to pass therethrough when the distal lip is aligned with the side opening.

Another aspect of the invention relates to a method of drilling through bone cement in a bone canal, the method comprising:
a) inserting an elongated cement drill into the bone canal, the elongated cement drill comprising a distal lip and a cylindrical centralizer having a central channel for the elongated cement drill to pass therethrough;
b) pushing the cylindrical centralizer into the bone canal, preferably using the elongated cement drill;
c) drilling the bone cement with the elongated cement drill supported and centered within the canal by the cylindrical centralizer while the bone cement freely rotates relative to the cylindrical centralizer; and
d) removing the cylindrical centralizer, preferably using the distal lip when removing the elongated cement drill from the bone canal.

Another aspect of the invention relates to a modular handle for use with tools for removing implants from bones, the modular handle comprising an elongated grip having a proximate end and a distal end, wherein the distal end comprises an adaptor configured to connect implant removal tools and the proximate end includes a T-shaped handle having a curved top surface configured to allow for impacting the top surface of the modular handle (e.g., a strike plate) and a bottom surface including a first bottom surface on a first side of the elongated grip and a second bottom surface on a second side of the elongated grip, wherein the first bottom surface and the second bottom surface each comprise a convex shape and the first bottom surface and the second bottom surface are configured for a user's upward hand movement against the first bottom surface and the second bottom surface.

Related methods of using and/or operation are also provided and/or described herein and are included in the invention. Other apparatuses, methods, systems, features, and advantages of the devices and systems for explanting hip and knee implants will be or become apparent to one with skill in the art upon examination of the following figures and detailed description. It is intended that all such additional apparatuses, methods, systems, features, and advantages be included within this description, be within the scope of the devices and systems for explanting or extracting the implants, and be protected by the accompanying claims.

DESCRIPTION OF THE INVENTION

Figure 1:
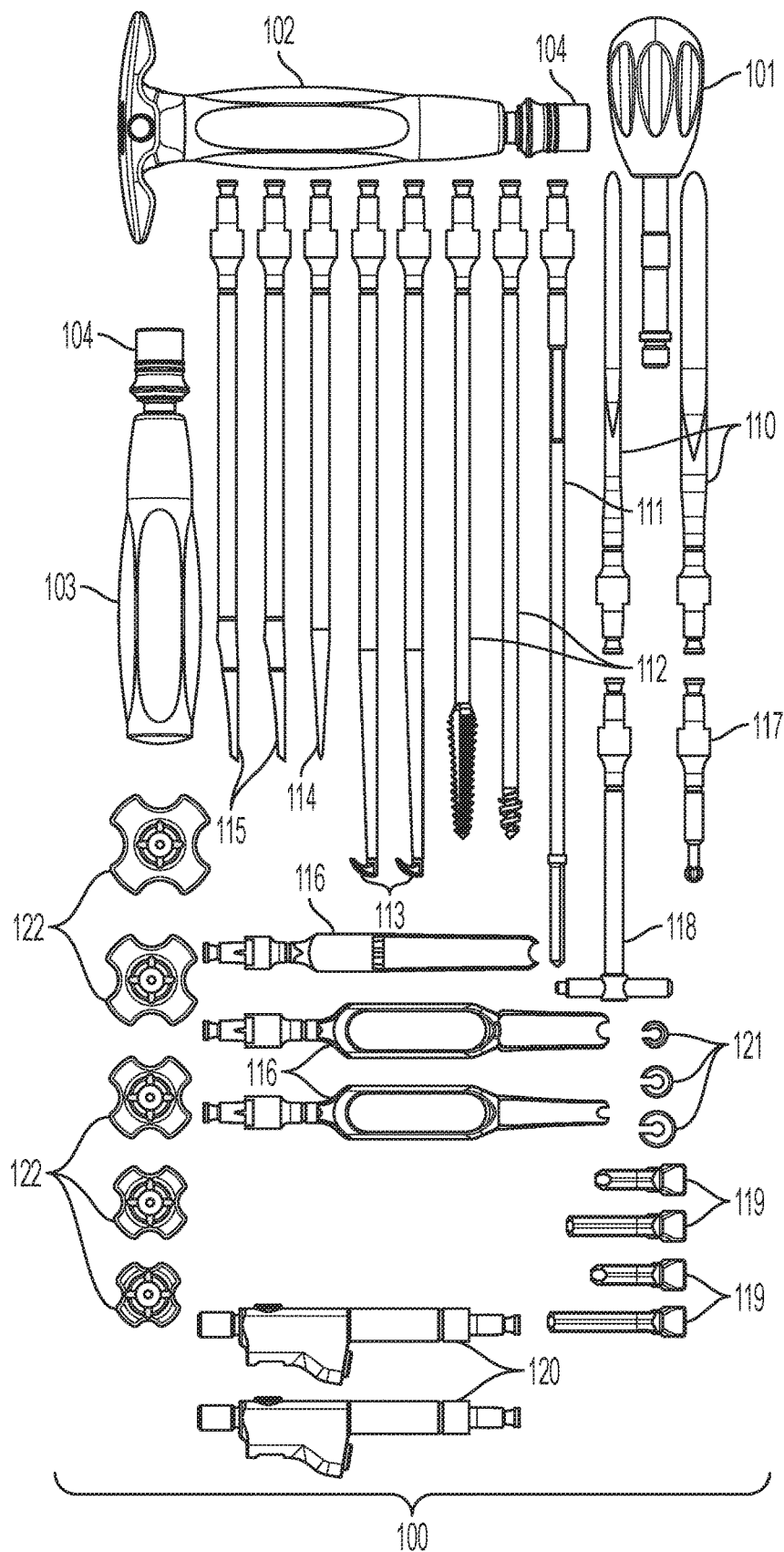
FIG. 1 is an illustration of a hip explant set according to one embodiment of the invention including modular handles and modular attachments for removing a femoral hip stem and acetabular cup implants.

The present invention can be understood more readily by reference to the following detailed description, examples, and claims, and figures, their previous and following description. In the following description, for purposes of explanation, specific details are set forth in order to provide a thorough understanding of different aspects of the present invention, including the figures. It will be evident, however, to one skilled in the art that the present invention as defined by the claims may include some or all of the features or embodiments herein described and may further include obvious modifications and equivalents of the features and concepts described herein. It is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting unless included in the claims.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "blade" or an "attachment" includes aspects having two or more such blades or attachments unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect and "about" is utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where the event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

One aspect of the invention relates to a set for removing a hip stem and acetabular cup implant from a femur or other implants, including two or more handles (preferably modular and interchangeable with other handles or tools) and two or more tools (preferably modular and interchangeable with other attachments). The modular and interchangeable handles and/to components allow the user to configure and re-configure the tool being used during the implant extraction method providing flexibility and quick adaptability as progress is made and/or different challenges are faced while performing the implant extraction and/or to better customize the instrument being used for the user, patient and implant.

One embodiment relates to a system for removing a hip stem and acetabular cup implant from a femur comprising:

(a) at least two modular handles and at least one modular slap hammer, and
(b) at least ten modular blades and/or at least two modular tools configured for facilitating the removal of the implant, wherein each modular blade and/or modular tool includes a proximal end configured to be attached to at least one modular handle or at least one modular slap hammer and a distal end including a cutting tip configured to cut through and/or remove bone growth into the implant thereby facilitating removal of the implant and/or removal of bone/cement adjacent the implant.

FIG. 1 illustrates one embodiment of the invention showing a hip implant extract set 100 including modular handles and modular attachments for removing a femoral hip stem and acetabular cup implant. FIG. 1 shows handles including a Tommy bar torque handle 101, extraction handle (with impact T-handle) 102 and short grip handle 103, each with an adaptor 104 (at distal end) for quick connecting to tool attachments. Each handle includes an ergonomic grip for user comfort and control. FIG. 1 further shows several modular tool attachments each including a quick connect adaptor for easy connection to a handle. The tools shown in FIG. 1 include chisel osteotomes 110, cement drills 111, tap tools 112, reverse curettes 113, V-osteotome(s) 114, scooped osteotome(s) 115, Femoral stem specific contoured osteotomes (media/lateral) 116, ball nose driver 117, acetabular cup fixation tester 118, acetabular cup cutter adjustable blades 119 and acetabular cup cutter shaft 120. Preferably, the set further includes one or more cement drill spacers 121 (U-shaped and top view of centralizers described below) and one or more acetabular cup cutter trial head attachments 122 (cross-shaped and top view). Preferably, the handle and tool components are enclosed in one or more containers.

The "modular" as used herein means a subcomponent of a surgical instrument or system that is interchangeable with other subcomponents, for example, modular handles that are interchangeable with other modular handles and/or different sized blades or surgical tools or instruments that are interchangeable with other surgical blades or tools using the same handle.

The term "quick connect" refers to Hudson connectors, and similar mechanical adaptors or connection means configured and adapted to easily connect one component to another without additional equipment or tools. For example, referring to FIG. 1, any of the handles shown can be quickly connected to any of the tools shown by simply joining the handle distal end with the proximate end of a tool components and pressing together to releasably attach the tool component to the handle; the components can also be quickly dis-assembled.

The term "configured for" as used herein means a component or element that is sized, shaped, configured, assembled or otherwise designed for the intended or predetermined purpose or use. For example, the phrase "knee claws configured to grasp the implant for femoral implant extraction" would be knee claws adapted to grasp the implant being removed.

According to one preferred embodiment, the set includes at least ten modular blades and/or at least two modular tools, more preferably further including a cup cutter having adjustable blades allowing for removal of different sized cups.

Figure 14:
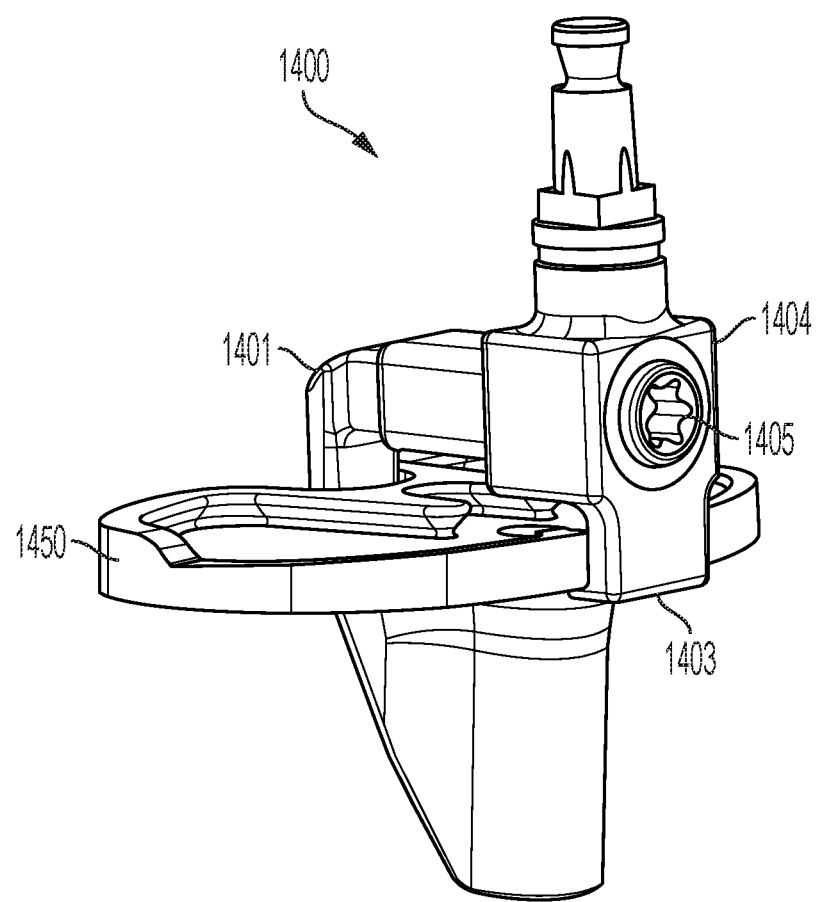
FIG. 14 is a side perspective view of a tibial knee plate remover attachment (with Tibial implant shown) according to another embodiment of the invention.

According to another preferred embodiment, the set includes at least five modular blades and/or at least two modular tools include knee claws configured to grasp the implant for tibial and femoral implant extraction. Preferably, the at least two modular tools include knee or other claws having one or more adjustable claw arm blades configured to grasp the implant for knee, tibial and femoral implant extraction. For example, the femoral claw (1121/1122) shown in FIG. 11 and the tibial claw adjustable claw arm/blade shown in FIG. 14 are identified as the adjustable claw/arm blades on either end of the instrument attachment.

According to another preferred embodiment, the at least ten modular blades and/or at least two modular tools include a hip femoral claw configured to grasp the hip femur to facilitate implant removal.

According to another preferred embodiment, the set further comprises a universal joint connected to the at least two modular handles or at least one modular slap hammer and attached to a drive mechanism to drive attachment of the hip femoral claw at an increased greater trochanter clearance. Preferably, the femoral claw is attached to a slap hammer. UJ is "universal Joint" allowing the thread to clamp the femoral claw to a femoral hip stem, where the force is directed into the neck of the femoral hip implant but driven at an angle to allow the thread to be driven at an angle that clears the greater trochanter. The universal joint is like that in a car, allowing torque at an angle out of alignment.

Preferably, the drive mechanism is at least one shaft or handle.

Figure 15:
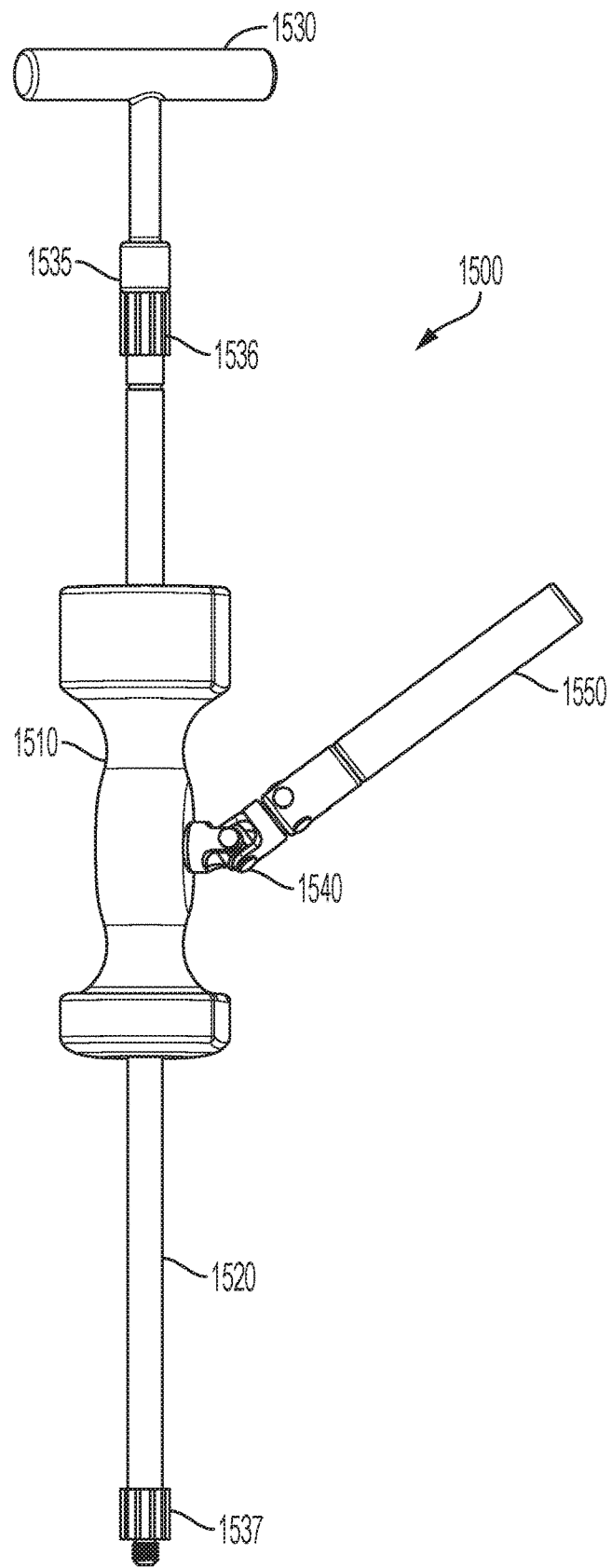
FIG. 15 is a side perspective view of a slap hammer instrument (both hammer mass and shaft) assembled with the: T-handle, U-joint, and extension grip according to another embodiment of the invention.

According to another preferred embodiment, the set and/or the at least ten modular blades and/or at least two modular tools include at least one slap hammer, preferably configured for providing at least a 6 lb increased delivered impact force. Preferably, further includes a universal joint handle and T handle as shown in FIG. 15 to deliver more mechanical advantage with more control.

According to another preferred embodiment, the at least ten modular blades and/or at least two modular tools include at least one cement drill and/or at least one centering spacer (or centralizer).

According to another preferred embodiment, the at least two modular handles or at least one modular slap hammer include at least one adaptor configured to connect the at least ten modular blades and/or at least two modular tools to the at least ten modular blades and/or at least two modular tools.

Figure 3:
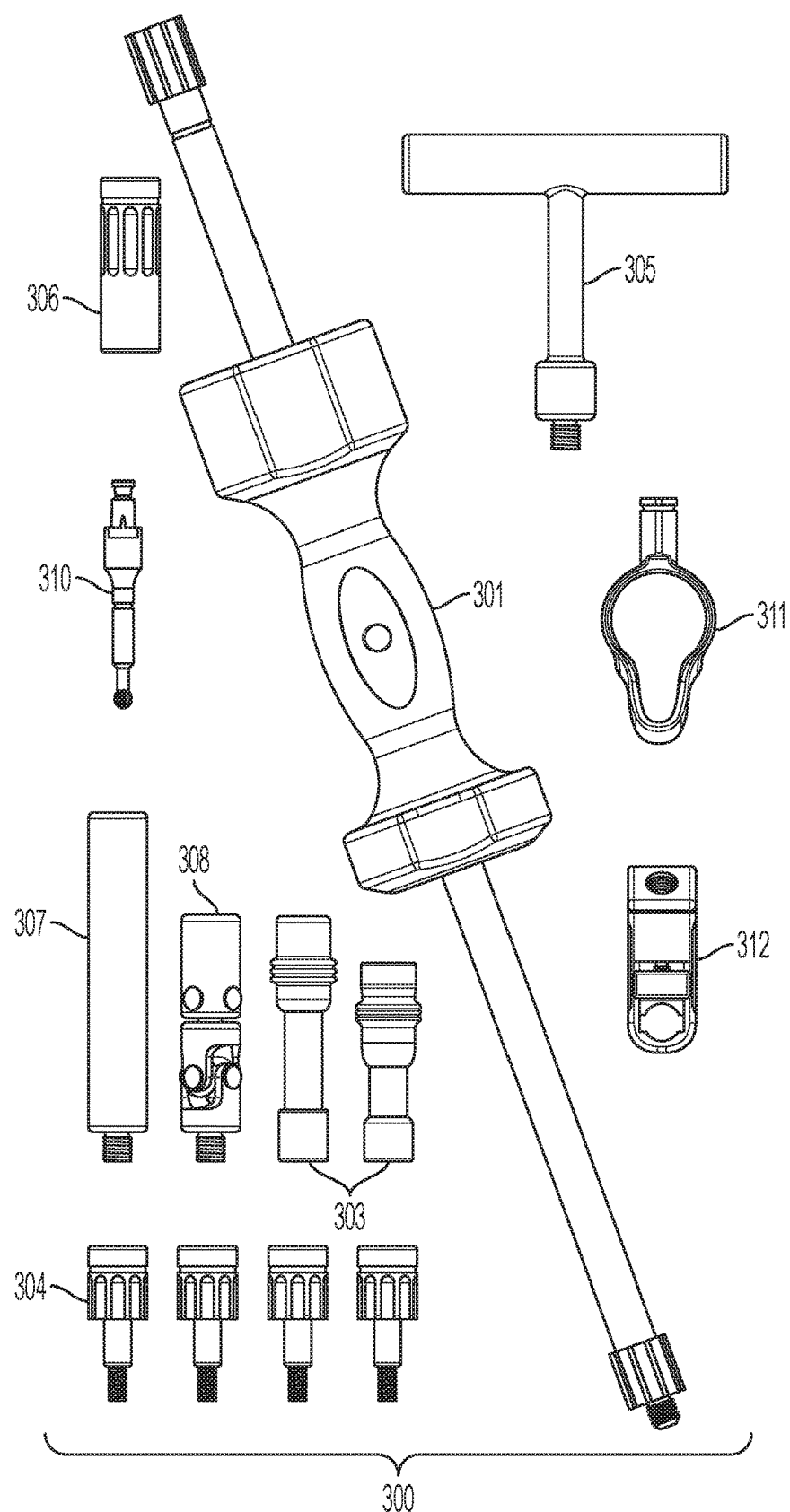
FIG. 3 is an illustration of an auxiliary set according to another embodiment of the invention which includes the slap hammer for high extraction forces, femoral stem implant connections, Hudson attachments, threaded stem implant attachments, T-handle, U-joint, and a ball nose driver (for tightening stem, femur, and tibial plate implant tool connections).

According to another preferred embodiment, the at least ten modular blades and/or at least two modular tools include at least one adaptor configured to connect the at least ten modular blades and/or at least two modular tools to the at least two modular handles or at least one modular slap hammer. Preferably, the at least one adaptor includes a Hudson connection or other quick-connect connection, for example, as shown in FIG. 3.

According to another preferred embodiment, the system, handle and/or the at least ten modular blades and/or at least two modular tools include at least one T-handle, U-joint, and universal driver for tightening stem, femur, and tibial plate implant connections. Preferably, the system or handle would include the T-Handle or U-Joint as the T handle and Universal Joint would be primarily used in conjunction with the slap hammer.

Another aspect of the invention relates to extraction sets or systems for removal of a tibial plate and femoral knee implant, the set or system including two or more handles (preferably modular and interchangeable) and two or more tool attachments.

One embodiment relates to a system for removal of a tibial plate and femoral knee implant comprising:
(a) at least one modular handle and at least one modular slap hammer, and
(b) at least three modular blades and/or at least three modular tools configured for facilitating the removal of the implant,
wherein each modular blade and/or modular tool includes a proximal end configured to be attached to at least one modular handle and/or at least one modular slap hammer and wherein a distal end of the modular blade or modular tool includes a cutting tip configured to cut through and/or remove bone growth into the implant thereby facilitating removal of the implant.

Figure 2:
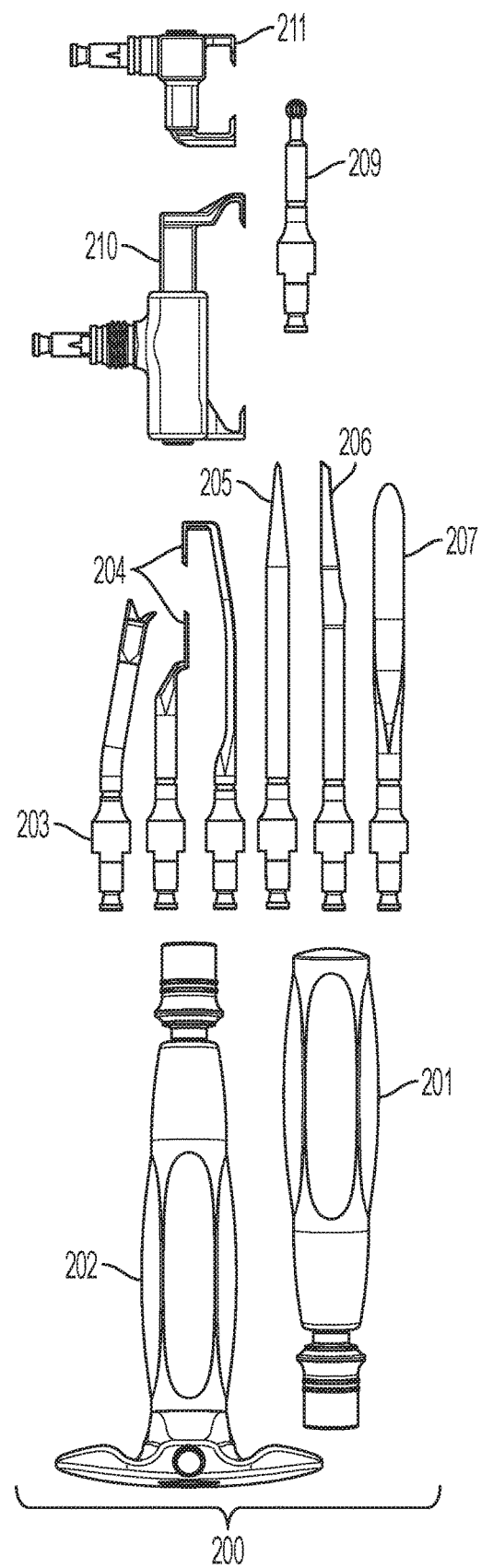
FIG. 2 is an illustration of knee explant set according to another embodiment of the invention including modular handles and modular attachments for removing a tibial plate and femoral knee implants.

FIG. 2 shows the knee set 200 which includes two modular handles (short grip handle 201 and extraction handle 202) and various attachments for removing a tibial plate and femoral knee implant and/or remove bone growth into the implant thereby facilitating removal of the implant (femoral implant removal osteotome 203, tibial implant removal osteomes 204, V-osteoome 205, scooped osteotome 206, chisel osteotome 207, ball nose driver 209, femoral implant attachment claw for removal 210 and tibial implant attachment claw for removal 211).

According to preferred embodiments, the at least three modular blades and/or at least two modular tools include a knee femoral claw and knee tibial claw which is configured to grasp the femoral and tibial components to facilitate implant removal.

FIG. 3 shows an auxiliary set 300 including the slap hammer 301 for high extraction forces, femoral stem implant connections (not shown), Hudson adapter attachments 303, threaded stem implant attachments 304, T-handle 305, claw adapter 306, threaded grip 307, U-joint adapter 308, and universal driver 310 for tightening stem, femur, and tibial plate implant connections. Auxiliary set 300 preferably further comprises femoral stem taper neck attachment 311 and femoral stem taper neck attachment 312.

Another embodiment of the invention relates to methods of using the systems or sets described above, the method comprising assembling an instrument configured to removing a hip stem and acetabular cup implant from a femur (or other implant) comprising:
(a) selecting at least one handle or slap hammer selected from at least two modular handles and at least one modular slap hammer,
(b) selecting a blade or tool selected from the at least ten modular blades and/or at least two modular tools; and
(c) assembling the selected handle or slap hammer with the selected blade or tool to form the instrument configured for facilitating the removal of the implant.

Preferably, each modular blade and/or modular tool includes a proximal end configured to be attached to at least one modular handle or at least one modular slap hammer and a distal end including a cutting tip configured to cut through and/or remove bone growth into the implant thereby facilitating removal of the implant.

Preferably, the handle or hammer is attached to the blade or tool using a quick connect (e.g., Hudson connect).

Preferably, the method further comprises using the instrument to remove cement and/or bone adjacent the implant.

Another aspect of the invention relates to extract systems including a handle reversibly coupled with a quick connect adaptor (preferably Hudson or similar mating interface) to an extraction attachment such as a blade.

Figure 4:
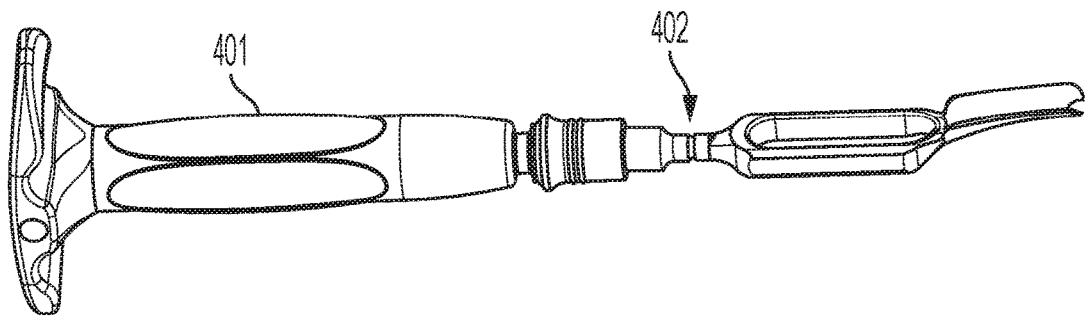
FIG. 4 is a side perspective view of a modular handle connected to a modular osteotome tool with a Hudson connection according to another embodiment of the invention.

FIG. 4 describes the handle 401 connected to a Hudson blade attachment (femoral stem osteotome) within the hip set 402. The handle design allows mallet impaction and extraction while maintaining connection to the handle and controlling the position of the osteotome to break bone ingrowth away from a femoral stem implant.

One embodiment of the invention relates to a modular tool for removing a femoral stem implant comprising:
(a) a modular handle configured for mallet impaction,
(b) at least one modular adaptor attached to the modular handle and configured to connect other modular components to the modular handle, and
(c) a modular component attached to the modular handle via the adaptor and configured for cutting bone/cement and/or removing the implant;
wherein the modular tool is configured for mallet impaction and extraction while maintaining connection to the modular handle and controlling the position of the modular component to break bone ingrowth away from the femoral stem implant.

Preferably, at least one modular adaptor is a Hudson or other quick connect adaptor.

Preferably, the modular component is an osteotome.

Another aspect of the invention relates to a quick-connect to threaded component adaptor having a threaded end to connect to a handle or impact device (e.g., slap hammer) and a quick-connect (e.g., Hudson) connector for attaching the tool (e.g., blade) to the adaptor.

Figure 5:
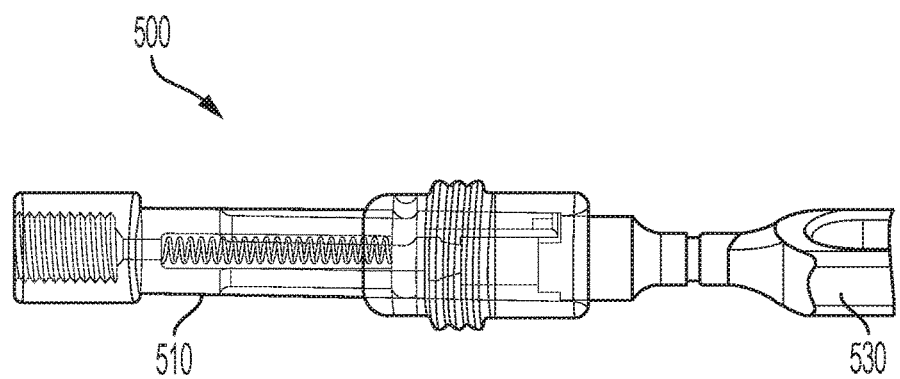
FIG. 5 is a side perspective view of a threaded adaptor (shown "see through") to connect a slap-hammer, T-handle, and U-joint to maneuver the Hudson attachment according to another embodiment of the invention.

FIG. 5 is a side perspective view of surgical tool 500 including a threaded adaptor 510 (shown "see through") to connect a slap-hammer, T-handle, and U-joint to maneuver the Hudson attachment 530.

Preferably, the adaptor includes an opening that slides open to allow the tool (e.g., blade) to slide into the adaptor and then the opening slides closed to retain the tool, as shown in FIG. 5 which describes the threaded adaptor to connect the slap-hammer, T-handle, and U-joint to maneuver the Hudson attachments.

One embodiment relates to a modular tool for removing an implant comprising:
(a) a modular handle, wherein the modular handle includes a threaded adaptor having at least one joint configured to connect to at least one modular component, and
(b) a modular extraction tool connected to the at least one joint;
wherein the extraction tool is configured to break bone ingrowth away from the implant and the at least one joint is configured to allow the modular extraction tool to maneuver relative to the modular handle.

Another aspect of the invention relates to a slap hammer shaft and mass, preferably having a quick connect adaptor on at least one end of the shaft, even more preferably both ends.

Figure 6:
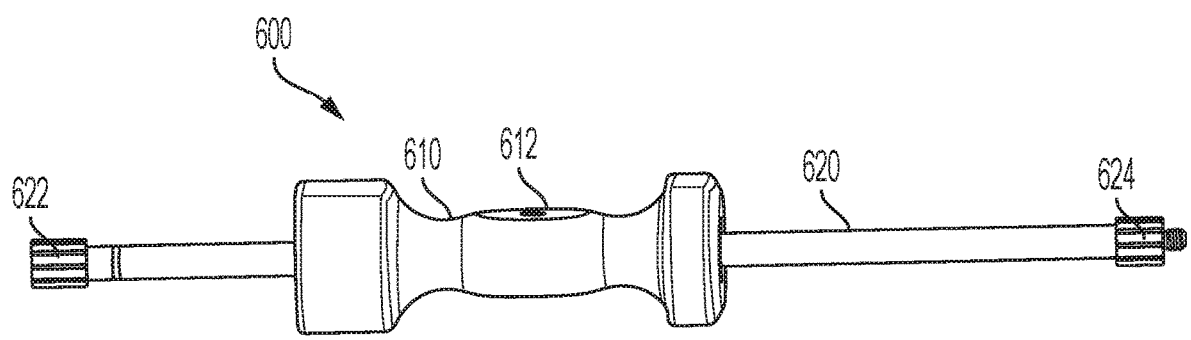
FIG. 6 is a side perspective view of a slap-hammer designed with an extended shaft length and handle mass to maximize extraction forces according to another embodiment of the invention.

FIG. 6 shows the slap-hammer instrument 600 designed with an extended shaft 620 and a handle hammer mass 610 to maximize extraction force. FIG. 6 also shows connection adaptors (622, 624) at each end of shaft 620. Adaptor 624 is configured to connect to an extraction tool or attachment (not shown) such as an osteotome, while adaptor 622 is configured to connect to a handle or grip (not shown in this FIG. 6 but is shown in FIG. 15 as item 1530). Handle mass 610 further includes threaded hole 612 to allow for the attachment of another handle or grip (not shown in this figure but shown in FIG. 15 as item 1540).

One embodiment of the invention relates to a modular tool for removing an implant comprising:
(a) a modular slap hammer mass, wherein the modular slap hammer mass has an inner channel extending from a first end to a second end of the modular slap hammer mass, and
(b) a shaft passing through the inner channel,
wherein the shaft has a first end configured to attach to an implant removal tool and the modular slap hammer mass is configured to slide along the shaft to create an impaction force to assist the implant removal tool remove the implant and/or removal of bone/cement adjacent the implant.

According to preferred embodiments, the shaft is a modular shaft.

According to preferred embodiments, the shaft is an elongated shaft.

According to alternative embodiments, the shaft is an extendible shaft, preferably a telescoping shaft.

Preferably, the shaft has a second end configured to attached to a tool or a handle.

Preferably, the modular slap hammer or mass is configured as a hand grip.

Preferably, the modular slap hammer is metal.

According to preferred embodiments, the slap hammer body (the central handle with mass) is constrained to the shaft with end caps (shown in FIG. 6 as having larger diameters than shaft).

According to preferred embodiments, the slap hammer is translated up the shaft to impact the cap to create an impaction force to assist in dislodging an implant that is connected to the slap hammer via one of the attachments.

Preferably, the mass of the central slide is significant (usually roughly 6 lbs.) to deliver a significant force, preferably the mass is between 4 and 8 lbs, more preferably between 5 and 7 and most preferred 6 lbs.

Preferably, the mass is modular and can be replaced with different sized masses or a mass having different size or shape.

Another aspect of the invention relates to systems or sets for the removal of an acetabular cup and methods of using the same.

One embodiment relates to a modular handle connected to the acetabular cup removal assembly attachment.

Figure 7:
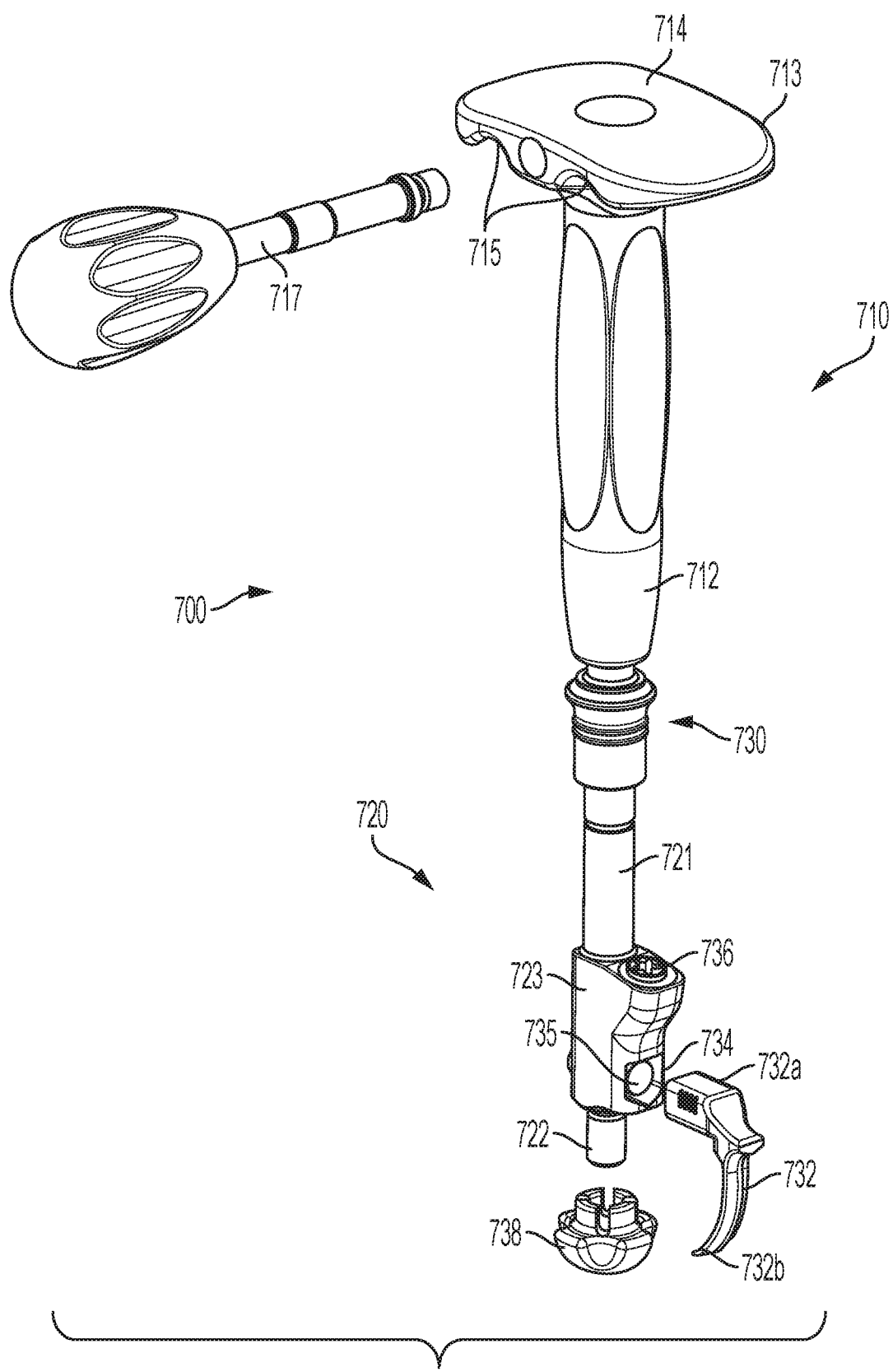
FIG. 7 is a side elevational perspective view of a modular handle connected to the acetabular cup removal assembly attachment according to another embodiment of the invention.

FIG. 7 shows an acetabular cup removal system 700 including a modular handle 710 connected to the acetabular cup removal assembly attachment 720 via a quick-connect connector 730.

Modular handle 710 includes ergonomic grip 712, T-shaped strike-plate top 713 with strike plate surface 714 (and ergonomic underside indentations 715 for upward hand movements), and quick-connect connector 730. System 700 preferably further includes a grip handle 717 attached to handle 710, preferably to strike-plate top 713, such as a short torque grip handle 717, as shown, to provide additional leverage, control and/or torque.

Acetabular cup removal assembly attachment 720 includes Acetabular cup shaft body 721 having a distal end 722 and housing 723 attached to shaft body 721, wherein housing 723 has reversibly attached thereto adjustable cup cutter blade 732. Blade 732 is shown disassembled and proximate blade connection opening 734 showing distal tip of blade adjustment screw 735. Housing 723 further comprises blade position locking mechanism 736 (shown as adjustable tightening screw). Acetabular cup removal assembly attachment 720 further includes cup cutter trial head attachment 738 (preferably reversibly connected to housing 723 or distal tip 722 of shaft body 721) configured to sit within interior of an acetabular liner or shell.

Blade 732 includes blade shoulder 732a configured to inserts into and connect to housing 723 via opening 734 and, preferably, contacts distal end of blade adjustment screw 735. Blade 732 further includes blade tip 732b. Preferably, blade 732 tapers from end of blade shoulder 732a to blade tip 732b (as shown in FIG. 7) to facilitate insertion to bone, cement and/or small space between implant and bone and/or to facilitate removing bone and/or cement. Another embodiment of the invention relates to blades comprising blade shoulder 732*a* and arm tapering to the blade tip 732*b* and configured for attachment to acetabular cup removal assembly attachments.

Figure 8:
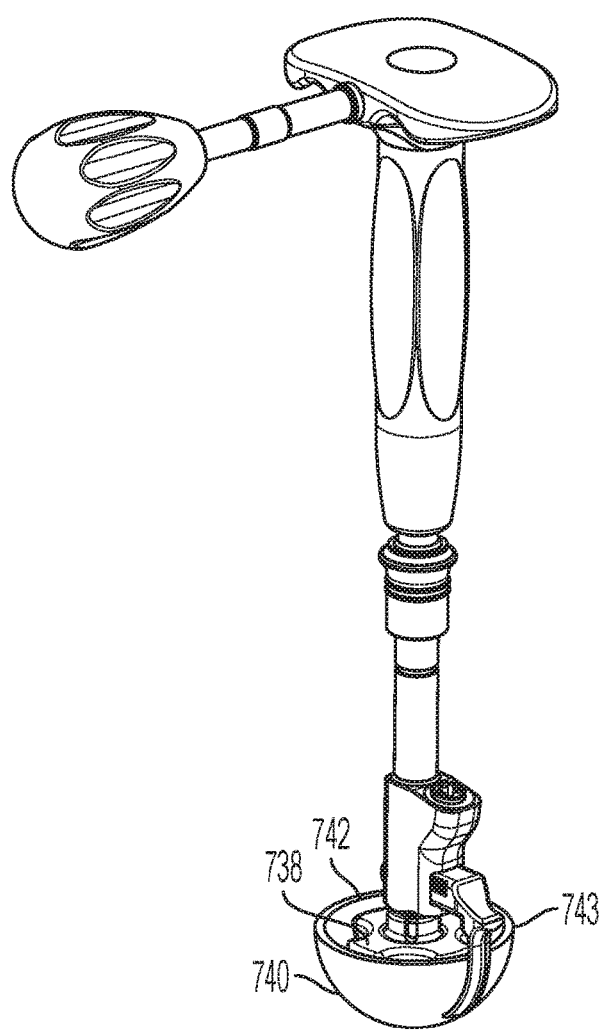
FIG. 8 is a side elevational perspective assembled view of the cup removal configuration of FIG. 7 with the acetabular shell implant shown to illustrate the contour between the blade and shell outer diameter according to this embodiment of the invention.
Figure 9:
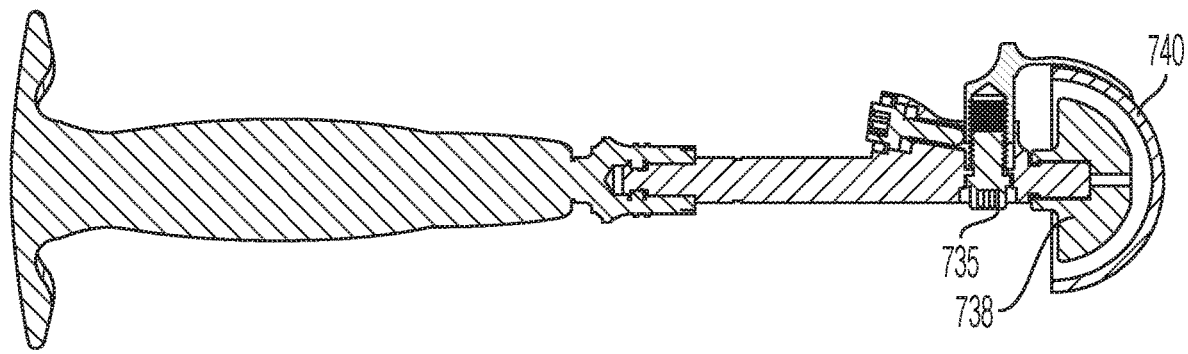
FIG. 9 is a side perspective section view of the acetabular cup removal assembly of FIG. 8 with the handle, Hudson adaptor, exchangeable head feature, adjustable blade feature, and blade position lock feature shown section according to another embodiment of the invention.

Preferably, the acetabular cup remover instrument 700 includes an interchangeable trial head attachment 738 for positioning and stabilizing the instrument within the interior 742 an acetabular liner or shell 740 (i.e., wherein the head size can be adjusted based on the implant size). Preferably, the acetabular cup remover also features an adjustable curved blade 732 positioned to track around the outer diameter 743 of the shell 740 to break the bone in-growth to facilitate removal of the implant. FIG. 8 shows the assembled view of the cup removal configuration with the acetabular shell implant 740 shown to illustrate the contour between the blade 732 and shell outer diameter 743 and head attachment 738 seated within shell 740. FIG. 9 shows a section view of the acetabular cup removal assembly 720 with the exchangeable trial head attachment 738, adjustable blade feature, and blade position lock 736 feature shown. As can be seen in FIG. 9, the adjustable curved blade 732 can translate perpendicular from shaft body 721 using blade adjustment screw 735 and is locked into position using position lock 736. Preferably, housing 723 includes a passthrough opening 734 (preferably perpendicular to shaft body 721) for the blade adjustment screw 735 and attaching blade shoulder 732*a* and an opening for position lock 736, as shown in FIG. 9. Preferably, position lock 736 presses onto or other locks onto blade shoulder 732*a* to lock the position of blade 732.

According to preferred embodiments, the blade is interchangeable with different sized blades and/or blades having different dimensions and curvature, so different blade lengths can be used for different sized and shaped implants and/or for different stages of the extraction process.

Preferably, the blade position may be adjusted to accommodate different shell diameters using the ball nose driver using the blade adjustment screw.

Preferably, a short torque grip handle 717 threads into the strike plate 713 of the modular handle 710 to provide additional torque and rotation leverage to maneuver the blade for breaking the implant to bone interface.

Another embodiment relates to an instrument for removal of an acetabular cup comprising:
(a) an elongated handle;
(b) an acetabular cup removal assembly attached to the elongated handle,
wherein the acetabular cup removal assembly includes: (i) an interchangeable head for positioning and stabilizing the instrument within an acetabular liner or shell and (ii) an adjustable curved blade positioned to track around the outer diameter of the acetabular liner or shell to break the bone in-growth.

Preferably, the acetabular cup removal assembly comprises a ball nose drive configured to move the adjustable curved blade from at least one first distance from the interchangeable head to at least one second distance.

According to one preferred embodiment, the adjustable curved blade is connected to the acetabular cup removal assembly by an adjustment mechanism comprising an adjustment screw configured to move the adjustable curved blade from at least one first distance from the interchangeable head to at least one second distance from the interchangeable head. Preferably, the adjustment mechanism further comprises a position lock or mechanism or means configured to secure the adjustable curved blade at a selected distance from the interchangeable head. Preferably, the position lock comprises a lock screw within a bore configured to secure the adjustable curved blade.

According to another preferred embodiment, the adjustment screw (preferably a ball nose driver) is aligned perpendicular to the handle and preferably, is configured to push the blade away from the shaft axis and/or from the head.

According to another preferred embodiment, the modular acetabular cup removal assembly comprises a housing including a head adaptor or opening to attach the interchangeable head and a blade adaptor or opening to attach the adjustable curved blade.

Preferably, the housing includes at least a first opening for the adjustment screw. Preferably, the housing further includes at least a second opening for the position lock.

Preferably, the housing further includes at least a third opening for the blade shoulder 732*a*. Preferably, the second opening and third opening are connected as shown in section FIG. 9.

According to another preferred embodiment, the handle is modular.

According to another preferred embodiment, the acetabular cup removal assembly is modular.

According to another preferred embodiment, the adjustable curved blade is interchangeable so different blades can be used and/or is adjustable to accommodate different shell diameters and/or shapes using a ball nose driver.

According to another preferred embodiment, the interchangeable head has a size and the size can be adjusted based on the implant size. For example, different sized and/or shaped cup cutter trial head attachments can be included in the system or set and used interchangeably depending on the size and/or shape of implant.

According to another preferred embodiment, the modular handle includes a strike plate. Preferably, the strike plate is T-shaped (with the top of the T forming the strike plate). More preferably, the underside of the strike plate is configured to upward motions to "lift" the instrument and includes curves to improve comfort and reduce slippage. For example, the underside surface 715 of strike plate 713 in FIG. 7 includes curves 715 on each side of T for improved hand fit and reduced slippage.

According to another preferred embodiment, the instrument further comprises a short handle adapted to be attached to the modular handle, preferably including an ergonomic grip. Preferably, the short handle is configured to provide additional torque and rotation leverage to maneuver the adjustable curved blade for breaking the implant to bone interface.

According to another preferred embodiment, the instrument further comprises an adjustable curved blade lock to secure the position of the blade.

Another embodiment of the invention relates to a method of removing an acetabular cup from a patient, the method comprising:
(a) assembling an instrument for removal of the acetabular cup including:
(1) an elongated handle; and
(2) an acetabular cup removal assembly attached to the elongated handle,
wherein the acetabular cup removal assembly includes:
(i) an interchangeable head for positioning and stabilizing the instrument within an acetabular liner or shell and (ii) an adjustable curved blade positioned to track around the outer diameter of the acetabular liner or shell to break the bone in-growth;
(b) positioning the head in the acetabular cup;
(c) inserting the adjustable curved blade around the outer diameter of the acetabular cup; and
(d) removing cement and/or bone growth adjacent the outer diameter of the acetabular cup by moving the blade.

Preferably, the method further comprises replacing the adjustable curved blade and/or the interchangeable head with replacement components (e.g., replacement blade and/or head).

Preferably, the method further comprises adjusting the position of the adjustable curved blade relative to the head, even more preferably by turning an adjustment device (e.g., an adjustment screw).

Another embodiment of the invention relates to a method of removing an acetabular cup from a patient, the method comprising removing cement and/or bone growth adjacent the outer diameter of the acetabular cup using the instrument(s) described here.

Preferably, the method further comprises replacing the adjustable curved blade and/or the interchangeable head with replacement components (e.g., replacement blade and/or head).

Preferably, the method further comprises adjusting the position of the adjustable curved blade relative to the head and/or shaft body axis.

Another embodiment of the invention relates to a method of removing an acetabular cup from a patient comprising:
(a) measuring the size and/or dimensions of the acetabular cup; and
(b) assembling an instrument for removal of the acetabular cup including:
  (1) an elongated handle; and
  (2) an acetabular cup removal assembly attached to the elongated handle,
wherein the acetabular cup removal assembly includes: (i) an interchangeable head selected for positioning and stabilizing the instrument within the acetabular cup liner or shell, and (ii) an adjustable curved blade selected to track around the outer diameter of the acetabular liner or shell to break the bone in-growth.

Preferably, the method further comprises inserting the adjustable curved blade around the outer diameter of the acetabular cup; and removing cement and/or bone growth adjacent the outer diameter of the acetabular cup.

Figure 10:
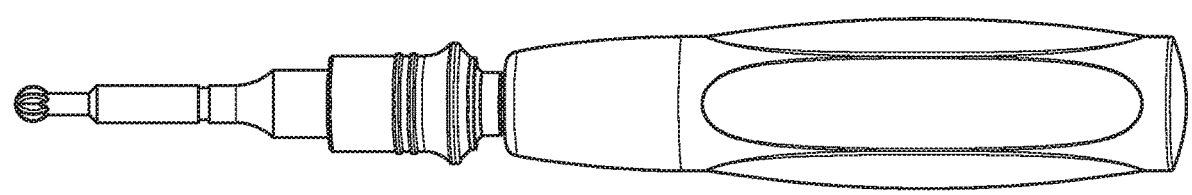
FIG. 10 is a side perspective view of a modular ball nose driver configured to adjust hexalobe screws at variable angles according to another embodiment of the invention.

Another aspect of the invention relates to a ball nose driver instrument including a modular handle with a "quick connect" to an interchangeable ball nose driver. FIG. 10 describes the ball nose driver that adjusts the hexalobe screws (not shown) at variable angles. The design of the driver allows for engagement of the driver and screw from various angles. The angle of attack to the screw interface can be off-axis to provide access when the screws are adjusted in-situ.

One embodiment relates to an instrument for removal of an implant, the instrument comprising:
(a) a modular handle; and
(b) a modular ball nose driver having hexalobe screws adapted to adjust at variable angles allowing for engagement of the modular ball nose driver and configured to connect to a modular surgical tool (e.g., hip cup cutter, Knee Femoral Claw, Knee Tibial Claw, Hip Femoral Claw, etc.).

Preferably, the angle of accessing the screw interface is off-axis to provide access when the screws are adjusted in-situ.

Another aspect of the invention relates to instruments for the removal of knee femoral component or implant having a handle and a femoral knee remover assembly.

Figure 11:
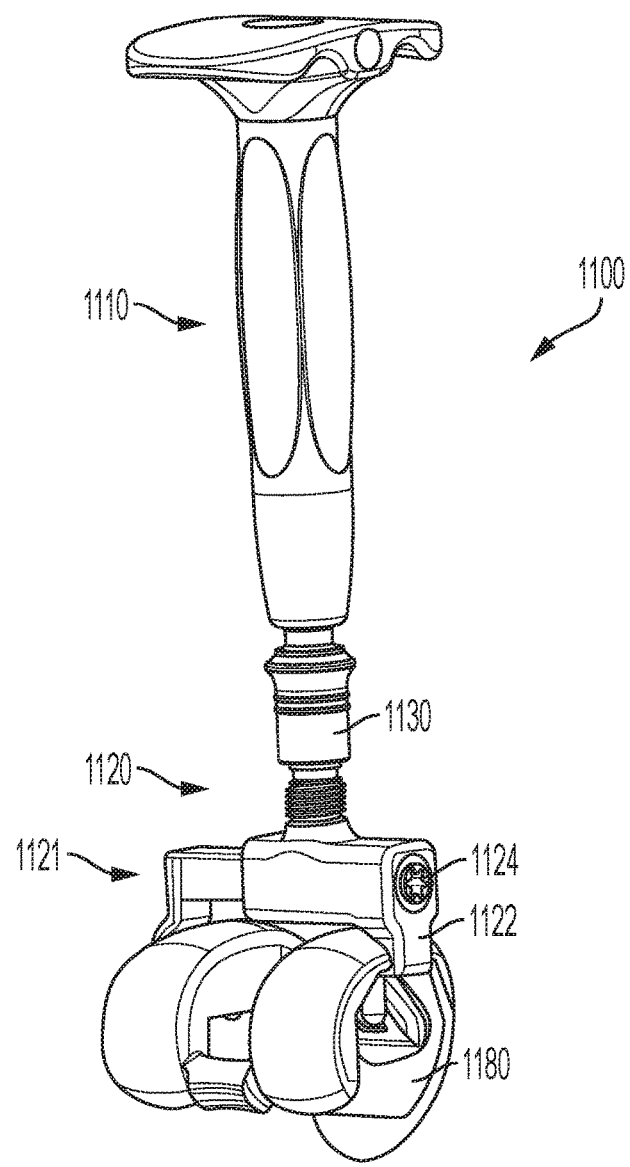
FIG. 11 is a side perspective view of a modular handle connected to the femoral knee remover attachment with implant shown according to another embodiment of the invention.

FIG. 11 shows an instrument 1100 including a modular handle 1110 connected to the femoral knee remover attachment 1120 via adaptor or connection means 1130. The femoral knee remover attachment 1120 preferably includes an adjustable arm blade 1121 to accommodate variable widths of implants 1180 and an opposing arm blade 1122. Preferably, adjustable arm blade 1121 is adjustable using an adjustment mechanism such as an adjustment screw 1124, as shown in FIG. 11.

According to preferred embodiments, the adjustable arm 1121 and opposing arm 1122 are designed or configured to clear the femur implant to be extracted and then compress under the implant to break the bone interface as they are fitted to size.

Figure 12:
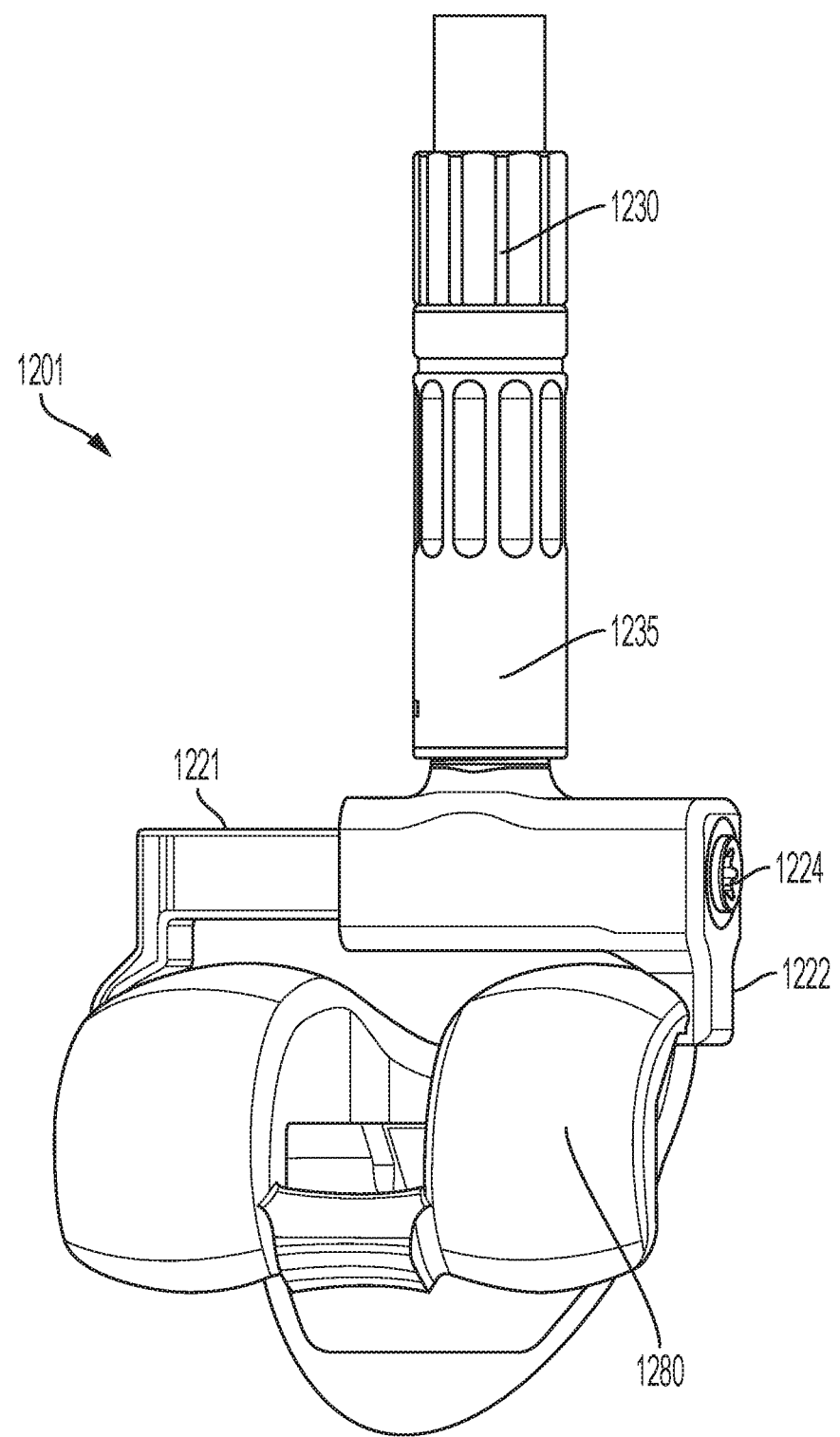
FIG. 12 is a perspective view of a femoral knee remover (with implant shown) when fitted with a threaded adaptor that allows it to mate directly to the slap-hammer according to another embodiment of the invention.

FIG. 12 shows a femoral knee remover 1201 including claw blades 1221, 1222 and adjustment screw 1224 according to another embodiment fitted with a threaded adaptor 1235 that allows it to mate directly to the slap-hammer (not shown) via the slap-hammer thread connection 1230.

According to preferred embodiments, a ball nose driver is used to adjust the width of the device by turning adjustment screw 2124. According to preferred embodiments, the femoral knee remover is fitted with a Hudson connection to attach to the modular handle. Preferably, there are also threads to allow it to connect directly to the for extreme extraction forces beyond the mallet forces used with the extraction handle.

Figure 13:
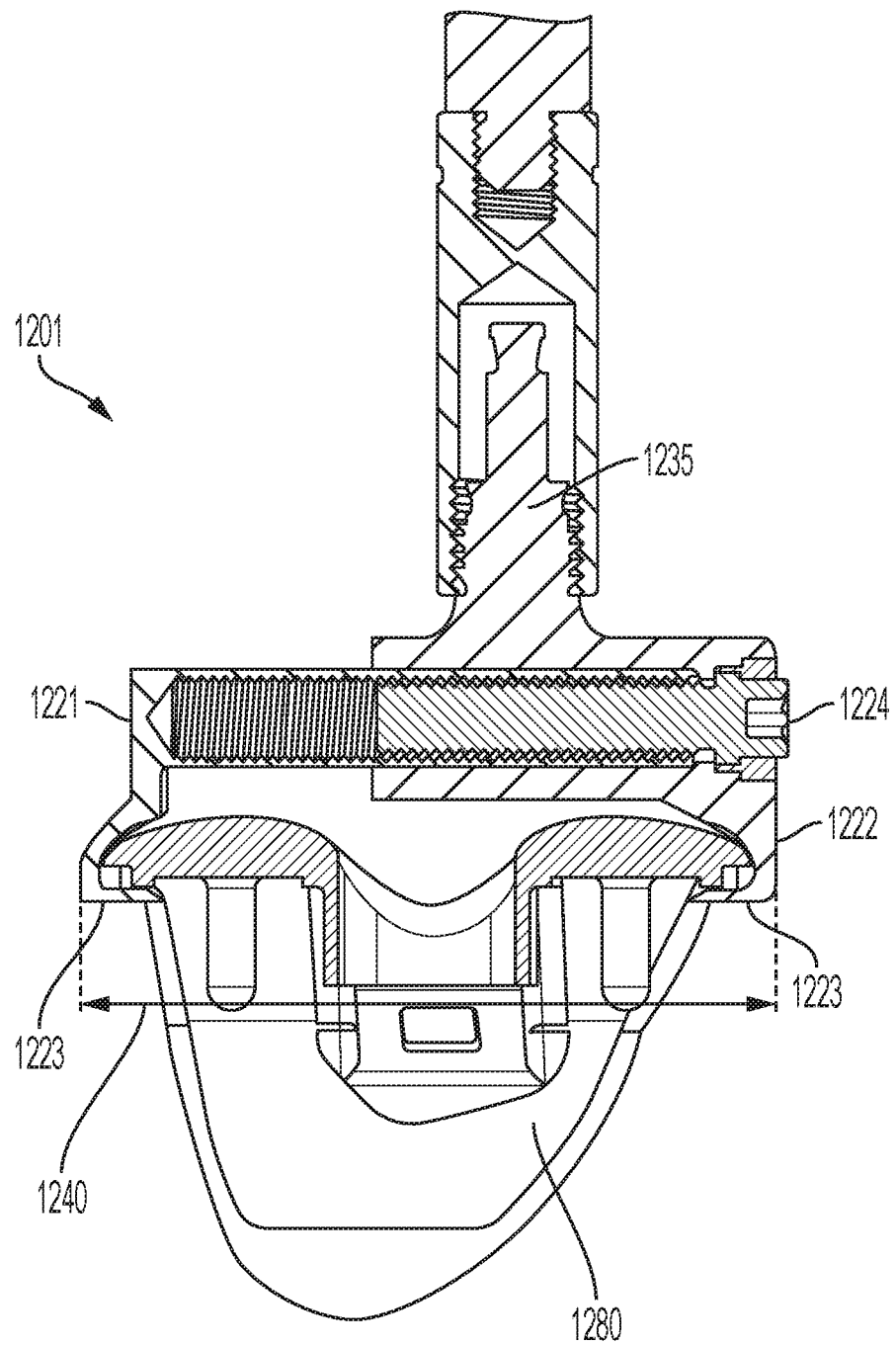
FIG. 13 is a section perspective view of a slap-hammer adaptor connection and an adjustable Femoral Knee Remover arm (with implant shown) according to another embodiment of the invention.

As stated above, FIG. 12 is a side perspective view of femoral knee remover 1201 according to another embodiment (with implant 1280 shown) when fitted with a threaded adaptor 1235 that allows it to mate directly to the slap-hammer (not shown) via slap hammer thread connection 1230. FIG. 13 show a section view of FIG. 12. FIG. 13 describes the section view of the slap-hammer adaptor connection and the adjustable Femoral Knee claw arm (including adjustment mechanism). The claws blades engage beneath the femoral knee implant to provide clearance and opposing forces with the blade edge for pulling the implant off the bone interface. Width adjustment screw 1324 can be turned to adjust the distance 1240 between the adjustable claw arm/blade and opposing claw arm/blade, that is distance 1240 can be increased or decreased to fit the implant.

One embodiment of the invention relates to an instrument for removal of a knee femoral component comprising:
(a) a handle having a strike plate at a first end and a second end including a connector;
(b) a femoral knee remover assembly configured to connect to the handle via the connector, wherein the modular femoral knee remover assembly comprises an adjustable arm blade configured to accommodate variable widths of implants.

According to preferred embodiments, the adjustable arm blade is adapted to clear a femur implant and compress under the femur implant to break bone interface.

According to preferred embodiments, the adjustable arm blade is modular and/or interchangeable. For example, to be replaced with an adjustable arm blade having a different grip configuration.

According to preferred embodiments, the instrument further comprises a ball nose driver configured to adjust the width of the adjustable arm blade.

According to preferred embodiments, the modular femoral knee remover assembly comprises a Hudson connection to attach to the modular handle.

Preferably, the instrument further comprises threads to allow it to connect directly to a tool for extreme extraction forces beyond the mallet forces used with the extraction handle.

According to preferred embodiments, the handle is modular.

According to preferred embodiments, the femoral knee remover assembly is modular.

According to preferred embodiments, the modular femoral knee remover assembly comprises a first adjustable arm blade and a second arm blade, each configured to clasp the knee femoral component. Preferably, the first adjustable arm blade is adapted to move relative to the second arm blade. Preferably, the first adjustable arm blade is moved using an adjustment screw. Preferably, the second arm is integral with the housing including the adjustment screw 1224.

According to preferred embodiments, the femoral knee remover assembly comprises a housing having at least one opening for an adjustment screw.

Preferably, the femoral knee remover assembly comprises a position lock to secure the position of the first adjustable arm blade relative to the second arm blade.

According to preferred embodiments, the housing includes the second arm blade. Preferably, the second arm blade is integral component of housing, while first arm blade can be adjusted relative to the housing.

Another embodiment of the invention relates to a modular femoral knee remover comprising a connecting shaft having a threaded adaptor configured to allow the modular femoral knee remover assembly to connect to a slap hammer.

According to preferred embodiments, the instrument further comprises an adjustable femoral knee remover arm. Preferably, the claws are configured to engage beneath the femoral knee implant (as shown in FIG. 13) to provide clearance and opposing forces with the blade edge for pulling the implant off the bone interface.

According to preferred embodiments, the modular femoral knee remover assembly comprises a first adjustable arm blade and a second arm blade, each configured to clasp the knee femoral component. Preferably, the first adjustable arm blade and/or the second arm blade includes a grip portion 1223 configured to engage beneath the femoral knee implant (as shown in FIG. 13).

According to preferred embodiments, the adjustable arm blade is adapted to clear a femur implant and compress under the femur implant to break bone interface.

According to preferred embodiments, the adjustable arm blade is interchangeable.

According to preferred embodiments, the remover further comprises a ball nose driver configured to adjust the width of the adjustable arm blade.

According to preferred embodiments, the modular femoral knee remover assembly comprises a Hudson connection to attach to the modular handle. Preferably having threads to allow it to connect directly to the for extreme extraction forces beyond the mallet forces used with the extraction handle.

According to preferred embodiments, the remover further comprises a modular handle.

According to preferred embodiments, the femoral knee remover assembly is modular.

According to preferred embodiments, the modular femoral knee remover assembly comprises a first adjustable arm blade and a second arm blade, each configured to clasp the knee femoral component. Preferably, the first adjustable arm blade is adapted to move relative to the second arm blade. Preferably, the first adjustable arm blade is moved using an adjustment screw or other adjustment means.

According to preferred embodiments, the femoral knee remover assembly comprises a housing having at least one opening for an adjustment screw.

According to preferred embodiments, the femoral knee remover assembly comprises a position lock to secure the position of the first adjustable arm blade relative to the second arm blade, preferably a position lock screw.

According to preferred embodiments, the housing includes the second arm blade. Preferably, the second arm blade is integral component of housing, while first arm is adjustable. Preferably, the housing also comprises the position lock.

Another aspect of the invention relates to instruments and systems including a tibial knee plate remover assembly having at least one adjustable arm blade adapted to clear a tibial implant and compress under the implant to break the bone/bone cement interface.

FIG. 14 describes the tibial knee plate remover attachment 1400. The tibial plate remover attachment 1400 preferably has an adjustable arm blade 1401 to clear the tibial implant 1450 when attached and compress under the implant to break the bone interface. The adjustable arm accommodates a range of tibial plate implant sizes. The ball nose driver is used to adjust the position of the arm. As shown in FIG. 14, the tibial knee plate remover attachment includes a first claw arm integral 1403 to the assembly housing 1404 and adaptor and a second adjustable claw arm 1401, preferably adjustable with a length adjustment screw 1405, preferably aligned parallel to the direction of movement for the second adjustable claw arm, as shown.

One embodiment of the invention relates to an instrument comprising a tibial knee plate remover assembly, wherein the tibial knee plate remover assembly comprises at least one adjustable arm blade adapted to clear a tibial implant and compress under the implant to break the bone/bone cement interface.

According to preferred embodiments, the adjustable arm blade accommodates a range of tibial plate implant sizes.

According to preferred embodiments, the instrument further comprises a ball nose driver configured to adjust the position of the adjustable arm blade.

According to preferred embodiments, the instrument further comprises at least one adaptor to connect the tibial knee plate remover assembly to a handle or slap hammer. Preferably, the at least one adaptor includes a Hudson connector.

According to preferred embodiments, the instrument includes threads below the Hudson adaptor (or other quick connect means) to attach the adaptor (described in FIGS. 12-13) to attach the tibial claw to a slap hammer.

Another aspect of the invention relates to slap hammers and methods of using the same.

FIG. 15 describes the slap hammer instrument 1500 including a slap hammer mass 1510 (black grip) and shaft 1520 is assembled with: T-handle 1530, U-joint 1540, and extension grip 1550. The T-handle 1530 preferably threads onto the end of the slap hammer shaft 1520 (via connections 1535/1536) to allow the user to stabilize the shaft of the slap-hammer during extraction. The U-Joint 1540 preferably threads into the slap hammer mass 1510 or shaft 1520 on one side and is threaded to the extension grip 1550 on the other side as shown.

According to preferred embodiments, the U-Joint allows the user to use a more natural arc motion of their arm when using the slap hammer. Specifically, the extension grip is allowed to rotate via the U-Joint allowing flexible configurations and/or orientations relative to the user, instrument and implant. This helps increase the force generated for extraction.

One embodiment of the invention relates to a slap hammer assembly for implant extraction comprising:
a) a slap hammer mass having a central channel;
b) a shaft passing through the central channel;
c) a T-handle connected to the shaft configured to allow the user to stabilize the shaft of the slap hammer during implant extraction;
d) a U-joint connected to the slap hammer; and
e) an extension grip, preferably modular, connected to the U-joint;

wherein the U-Joint connects to, preferably threads into, the slap hammer on one side and connects to, preferably is threaded to, the extension grip on the other side.

According to preferred embodiments, the U-joint is modular and interchangeable with other joints. Alternatively, the U-joint is permanently attached to the slap hammer mass.

According to preferred embodiments, the U-joint is configured to allow a user a more natural arc motion of the user's arm when using the slap hammer to increase the force generated for extraction.

Preferably, shaft 1520 includes an adaptor 1536 at one end for connecting to the T-handle and adaptor 1537 for connecting to a tool or attachment (not shown).

Figure 16:
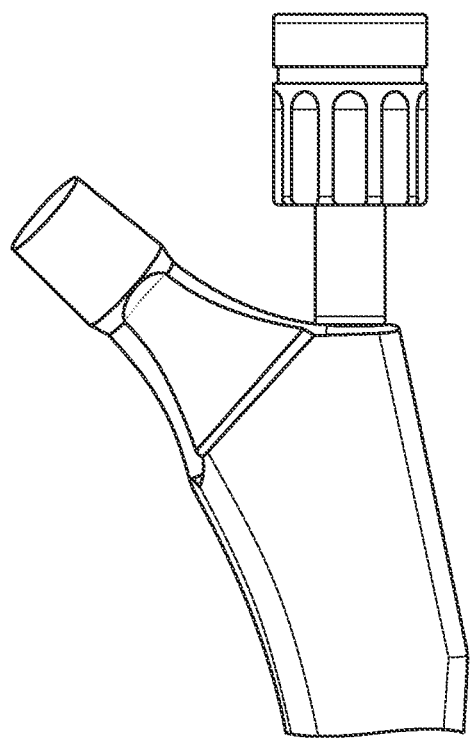
FIG. 16 is a side perspective view of a femoral stem threaded adaptor according to another embodiment of the invention.

Another aspect of the invention relates to femoral stem threaded adaptors and methods of using the same. FIG. 16 describes the femoral stem threaded adaptor according to one preferred embodiment. On one end, a set of male threads engage with the female threads on the implanted femoral stem. On the other end, a set of female threads allow for engagement with the slap-hammer for extreme extraction forces to remove the implant.

One embodiment relates to a femoral stem threaded adaptor comprising a first end having a first set of threads adapted to engage with corresponding threads on an implanted femoral stem and a second end having a second set of threads configured to allow the adaptor to engage a tool (e.g., slap hammer) for extraction of the implant.

Figure 17:
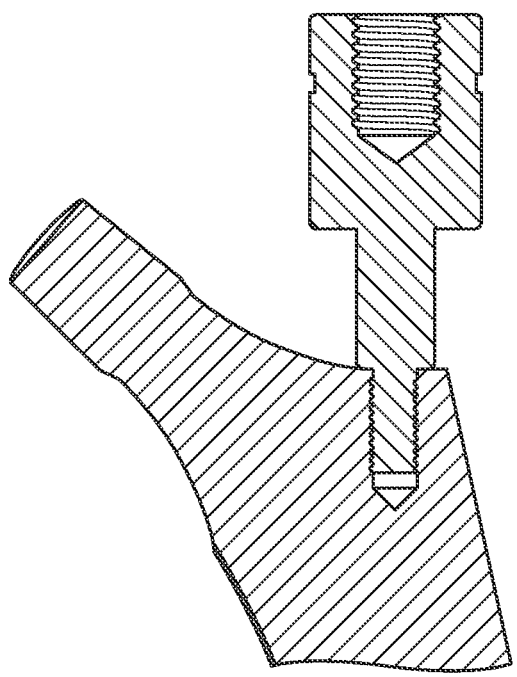
FIG. 17 is a side perspective section view of the adaptor of FIG. 16.

Preferably, the first end is cylindrical having a first diameter and the second end is cylindrical having a second diameter greater than the first diameter. For example, as shown in FIGS. 16-17. FIG. 17 describes the section view of the male threaded stem adaptor end assembled to the stem implant and the second female threaded end for connecting to a handle, grip, hammer or other instrument.

Another aspect of the invention relates to a stem yoke attachment and methods of using the same.

Figure 18:
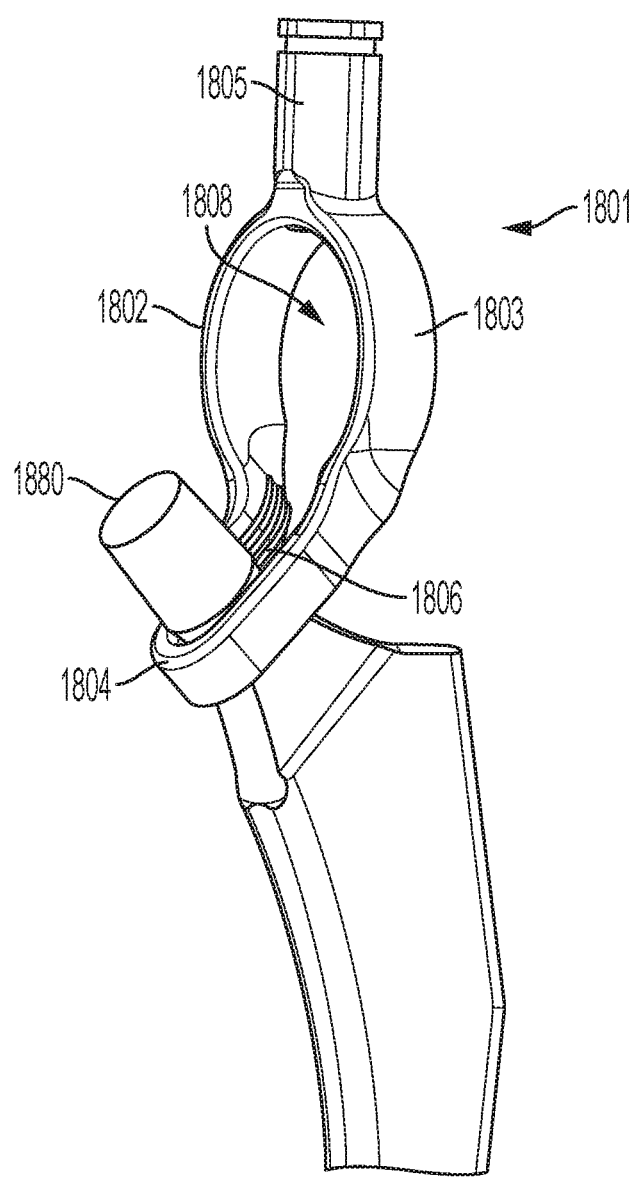
FIG. 18 is a front side perspective section view of a stem yoke grabber attachment according to another embodiment of the invention.

FIG. 18 illustrates a stem yoke attachment 1801 according to one embodiment of the invention. On one end, the hoop 1802 contours to the stem taper to lock into the stem neck 1880 and on the other end 1805 it is configured to allow for attachment to the slap-hammer (not shown) to extract the implant. Specifically, referring to FIG. 18, the hoop 1802 contours from a wide hoop section 1803 providing a large space 1808 to a narrower hoop distal end section 1804 to enable the attachment 1801 to latch onto stem 1880. The yoke preferably has sharp teeth 1806 within the inner surface of narrower hoop distal end section 1804 to grip the stem neck 1880. The yoke is preferably angled at a typical stem neck angle for the slap-hammer shaft to be aligned with the stem body for optimum removal efficiency. According to preferred embodiments, the yoke also allows for assembly with a stem that has a one-piece integrated head, allowing the hoop section to fit over a fixed cylindrical ball.

Another embodiment of the invention relates to a stem yoke attachment having a first end comprising a hoop configured to contour to a stem taper to lock onto the stem neck and a second end adapted to attach to a slap hammer having a shaft.

Preferably, the hoop is curved or angled at a typical stem neck angle for the slap hammer shaft to be aligned with the stem for optimum removal efficiency.

Preferably, the hoop comprises an inner surface having teeth adapted to grip the stem neck.

Preferably, the stem yoke attachment is adapted to allow for assembly with a stem that has a one-piece integrated head, allowing the hoop to fit over a fixed cylindrical ball.

Figure 19:
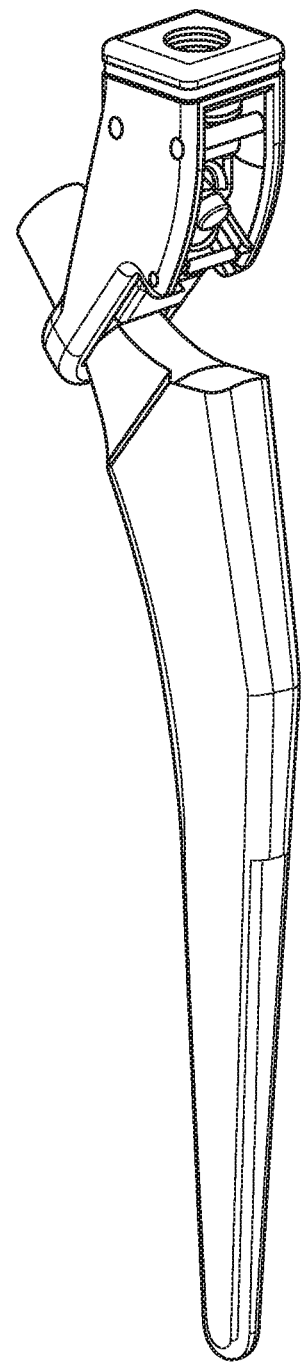
FIG. 19 is a rear side perspective section view of a stem grabber according to another embodiment of the invention.

FIG. 19 shows the back view of a stem grabber attachment according to another embodiment and illustrates that the attachment tightens onto the stem neck. The stem grabber preferably has sharp teeth that lock into the stem neck. The threaded side of the stem grabber is meant to be engaged with threaded slap hammer. The slap hammer can then then be employed to extract the femoral stem. The stem grabber is preferably angled at a typical stem neck angle for the slap-hammer shaft to be aligned with the stem body for optimum removal efficiency.

Figure 20:
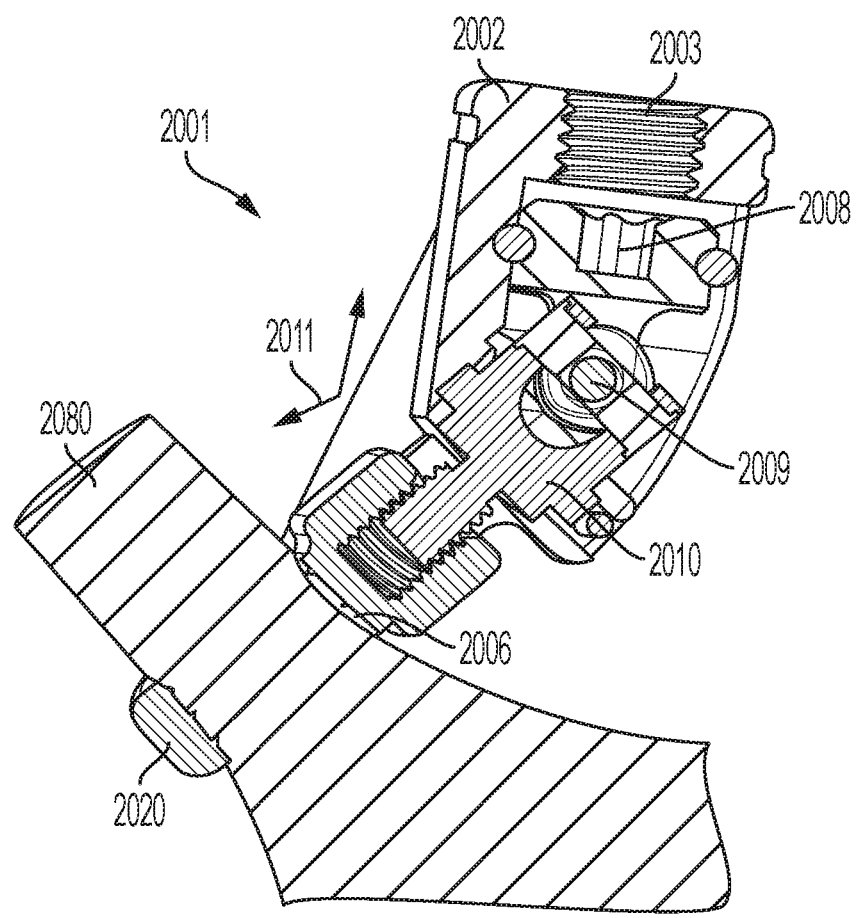
FIG. 20 is a side perspective section view of the stem grabber attachment of FIG. 19.

FIG. 20 describes the section view of stem grabber attachment 2001 according to another embodiment of the invention. The teeth 2006 are tightened with the ball nose driver that torques the U-joint 2009 to drive the lower U joint component 2010 which rotates to translate the lower Femoral Hip grabber Block 2006 to lock onto the stem neck 2080 as shown in the section view against the front lip of the stem grabber 2020.

Another embodiment of the invention relates to a stem grabber having a first end comprising an adjustable hoop 2020 configured to contour to a stem taper to adjust and lock onto the stem neck 2080 and a second end 2002 adapted to attach to a slap hammer having a shaft via threaded opening 2003.

Preferably, the adjustable hoop is adapted to tighten onto a stem neck.

Preferably, the adjustable hoop has an interior surface comprising teeth 2006 that lock into the stem neck.

Preferably, the second end is adapted to engage with a threaded slap hammer configured to extract the femoral stem.

Preferably, the stem grabber is angled at a typical stem neck angle 2011 for the slap-hammer shaft to be aligned with the stem body for optimum removal efficiency.

According to preferred embodiments, the stem grabber comprises a threaded interior piston 2010 within grabber 2001 that is configured to be turned and thereby adjust the size of the adjustable loop 2020 as shown in FIG. 20.

Preferably, the stem grabber further comprises a U-joint 2009 and a ball nose driver 2008 configured to torque the U-joint to adjust the adjustable hoop to lock onto the stem neck.

Preferably, the U-joint is configured for tightening the hoop on the femoral stem while minimizing the space needed to introduce the device while maintaining the appropriate angle 2011 to attach the slap hammer.

According to preferred embodiments, the anatomy of the hip (namely the greater trochanter) is positioned lateral to the device and limits the size and configuration that would fit the anatomy.

Another embodiment of the invention relates to a method of using a stem grabber having an adjustable hoop configured to contour to a stem taper, the method comprising:

(a) placing the adjustable hoop around the stem; and (b) adjusting the adjustable hoop to latch onto the stem.

Preferably, the method further comprises locking the adjustable hoop after the adjustable hoop is latched onto the stem.

Preferably, the method further comprises attaching a slap hammer having a shaft to the stem grabber.

Another aspect of the invention relates to systems and/or instruments including a cement drill and a centering guide (and/or cement drill spacers).

Figure 21A:
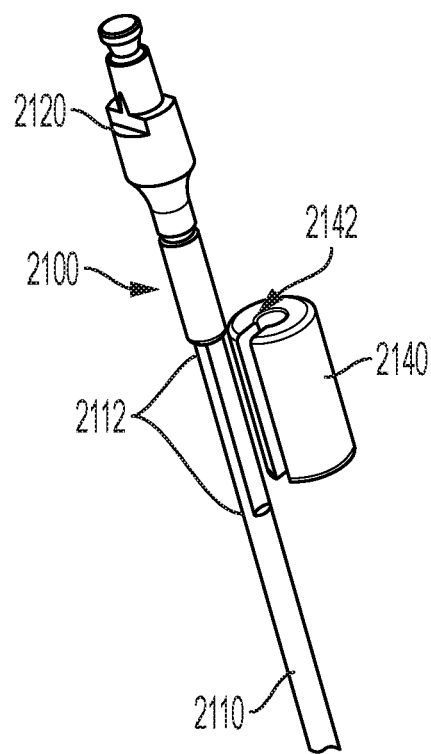
FIGS. 21A-C is a side perspective views of a cement drill and centering guide according to another embodiment of the invention.
Figure 21B:
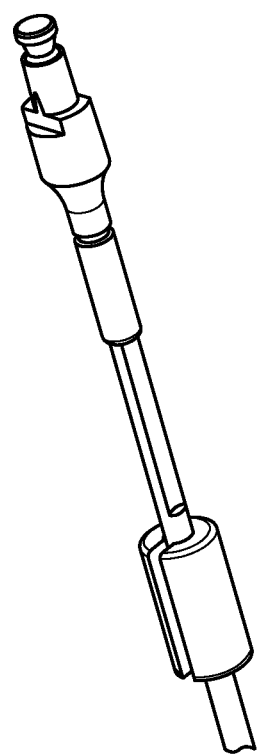
Figure 21C:
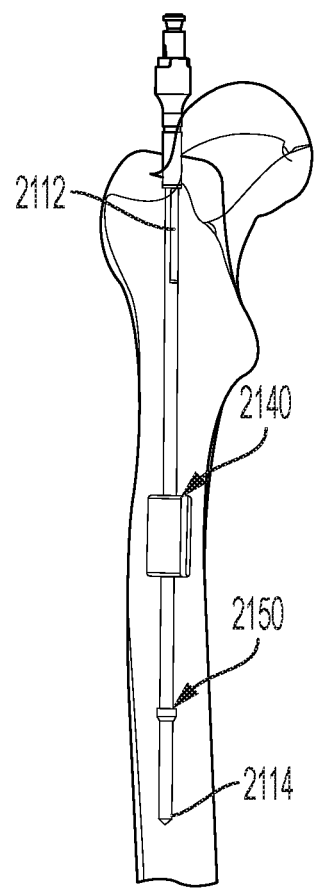

FIGS. 21A-C shows a cement drill system 2100 configured to drill through bone cement remaining in the canal during revision hip surgery where a cemented hip stem has been removed. FIG. 21A shows the cement drill 2110 and disassembled C-shaped cylindrical centralizer 2140 according to one embodiment. Cement drill 2110 includes adaptor 2120 for attaching to a drill or other device (not shown). According to preferred embodiments, the system 2100 can include two or more the cement centralizers 2140 having different diameters to match different femoral canal diameters and/or canals with varying diameters. As shown in FIG. 21A, the centralizer is preferably a "c" shaped and cylindrical with a narrow flat opening 2142 along one side as shown. The centralizer is slid onto the cement drill in the flat portion 2112 of the drill shown as shown in FIG. 21B and then slid down onto the cylindrical shaft where it is retained by distal lip 2150 (shown in FIG. 21C). The drill is then inserted into the femoral shaft to drill through any remaining cement as shown in FIG. 21C. The cement drill centralizer helps keep the drill centered within the canal while allowing the drill to rotate freely. As shown in FIG. 21C, the drill includes a distal lip or protrusion 2150 near the distal end 2114 of the drill configured to retain the drill centralizer when the drill is removed. The distil tip 2150 can be a ring around the diameter of the drill or a tab or other protrusion to catch the centralizer as the drill is removed from the canal.

One embodiment of the invention relates to a cement drill system for drilling through bone cement within a canal within a bone, the cement drill system comprising:

a) an elongated cement drill having a proximal end including an adaptor for connecting the cement drill to a handle or drilling device, a distal end comprising a distal lip on at least one side of the elongated cement drill and a narrower diameter region between the proximate end and the distal lip; and b) at least one cylindrical centralizer having a central channel for the elongated cement drill to pass therethrough and a side opening along the length of the centralizer and configured to allow the centralizer to slid onto the narrower diameter region of the cement drill and slid down below the narrower diameter region to stabilize the cement drill.

Preferably, the position of the distal lip along the elongated cement drill is adjustable.

Preferably, the size of the distal lip can be adjusted.

Preferably, the adaptor 2120 is a quick connect coupling (e.g., using a Hudson connect).

Preferably, the system comprises two or more cylindrical centralizers having different diameters, lengths and/or shapes.

Preferably, the at least one cylindrical centralizer has a proximate end (i.e., top end) and distal end (i.e., bottom end), wherein the proximate end is tapered to facilitate removal of the at least one cylindrical centralizer from the canal.

According to preferred embodiments, the narrower diameter region includes protruding flats or lips on the proximal portion or top portion of the elongated cement drill to allow the at least one cylindrical centralizer to be pushed into the canal by the drill.

Preferably, the protruding flats can be rotated to align with the side opening to allow the drill to slide and rotate freely relative to the at least one cylindrical centralizer.

According to preferred embodiments, the centralizer comprises a center portion and an outer portion, wherein the center portion is stiffer than the outer portion. Preferably, the outer surface of centralizer is flexible allowing for minor deformation to accommodate variations within the bone canal, while the core of the centralizer is stiff providing support for the drill.

Another embodiment of the invention relates to a cement drill system for drilling through bone cement within a canal within a bone, the cement drill system comprising:

a) an elongated cement drill having a proximal end including an adaptor for connecting the drill to a handle or drill device and a distal end comprising a distal lip on a side of the elongated cement drill; and b) at least one cylindrical centralizer having a central channel for the elongated cement drill to pass therethrough and a side opening along the length of the centralizer and configured to allow the distil lip to pass therethrough when the distal lip is aligned with the side opening.

Preferably, the distal lip is configured to remove the cylindrical centralizer from the canal of the bone when the distal lip is not aligned with the side opening.

Preferably, the system comprises at least two cylindrical centralizers.

Another aspect of the invention relates to a method of drilling through bone cement in a bone canal, the method comprising:

a) inserting an elongated cement drill into the bone canal, the elongated cement drill comprising a distal lip and a cylindrical centralizer having a central channel for the elongated cement drill to pass therethrough;

b) pushing the cylindrical centralizer into the bone canal using the elongated cement drill;

c) drilling the bone cement with the elongated cement drill supported and centered within the canal by the cylindrical centralizer while the bone cement drill freely rotates relative to the cylindrical centralizer; and d) removing the cylindrical centralizer using the distal lip when removing the elongated cement drill from the bone canal.

Another embodiment of the invention relates to a method of drilling through bone cement in a bone canal, the method comprising:

a) inserting an elongated cement drill into the bone canal, the elongated cement drill comprising a distal lip; and b) drilling the bone cement with the elongated cement drill supported and centered within the canal by a cylindrical centralizer within the canal while the bone cement drill freely rotates relative to the cylindrical centralizer.

Preferably, the method further comprises removing the cylindrical centralizer using the distal lip when removing the elongated cement drill from the bone canal.

Another embodiment relates to an elongated cement drill for drilling through bone cement within a canal within a bone, the cement drill having a proximal end including an adaptor for connecting the drill to a handle and a distal end comprising a distal lip on at least one side of the elongated cement drill and further comprising a narrowed portion along the length of the elongated cement drill between the proximal end and the distal lip.

Preferably, the distal lip is ring-shaped and around the circumference of the cement drill.

Preferably, the narrowed portion comprises two parallel planar surfaces and two end sides (ends sides can be rounded or flat).

Preferably, the narrowed portion is cylindrical and has a diameter less than the diameter of the elongated cement drill.

Preferably, the narrowed portion has a length along the elongated cement drill ranging from 0.5 to 4 inches, preferably 1-2 inches.

Another aspect of the invention relates to a T-shaped handle providing adaptable uses and configurations. For example, FIG. 11 shows a T-shaped handle connected to a femoral knee remover assembly. Preferably, the T-shaped handle comprises a quick connect (e.g., Hudson adaptor) at its distal end for attaching to attachments (e.g., the attached femoral knee remover assembly shown in FIG. 11).

One embodiment relates to a modular handle for use with tools for removing implants from bones, the modular handle comprising an elongated grip having a proximate end and a distal end, wherein the distal end comprises an adaptor configured to connect implant removal tools and the proximate end includes a T-shaped handle having a curved top surface configured to allow for impacting the top surface of the modular handle (preferably including a strike plate) and a bottom surface including a first bottom surface on a first side of the elongated grip and a second bottom surface on a second side of the elongated grip, wherein the first bottom surface and the second bottom surface each comprise a concave shape and/or the first bottom surface and the second bottom surface are configured for a user's upward hand movement against the first bottom surface and the second bottom surface.

Preferably, the elongated grip is cylindrical.

Preferably, the elongated grip comprising two or more convex regions along the length of the elongated grip to improve grip.

Preferably, the elongated grip comprising two or more concave regions along the length of the elongated grip to improve grip.

Preferably, the elongated grip comprises a textured surface to improve grip.

Preferably, the elongated grip (shown as green in FIG. 11) comprises metal and/or plastic, more preferably comprises silicone molded around a metal core.

Preferably, the T-shaped handle strike plate comprises a metal, more preferably the strike plate portion is made of high strength stainless steel.

Preferably, the elongated grip has a length ranging from 3 in to 7 in.

Preferably, the modular strike plate has a width ranging from 1.5 in to 5 in.

Preferably, the modular handle overall length (handle, strike plate and Hudson) ranges from 3 in to 9 in.

The scope of the present devices, systems and methods, etc., includes both means plus function and step plus function concepts. However, the claims are not to be interpreted as indicating a "means plus function" relationship unless the word "means" is specifically recited in a claim, and the claims are to be interpreted as indicating a "means plus function" relationship where the word "means" is specifically recited in a claim. Similarly, the claims are not to be interpreted as indicating a "step plus function" relationship unless the word "step" is specifically recited in a claim, and the claims are to be interpreted as indicating a "step plus function" relationship where the word "step" is specifically recited in a claim.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An instrument for removal of an acetabular cup, the instrument comprising:
   (a) an elongated handle; and
   (b) an acetabular cup removal assembly attached to said elongated handle,
   wherein said acetabular cup removal assembly includes: (i) an interchangeable head for positioning and stabilizing the instrument within an acetabular liner or shell and (ii) an adjustable curved blade positioned to track around the outer diameter of the acetabular liner or shell to break the bone in-growth and/or cement,
   wherein said adjustable curved blade is connected to said acetabular cup removal assembly by an adjustment mechanism comprising an adjustment screw configured to move the adjustable curved blade from at least one first distance from said interchangeable head to at least one second distance from said interchangeable head; and
   wherein said adjustment mechanism further comprises a position lock configured to secure said adjustable curved blade at a selected distance from said interchangeable head.

2. The instrument of claim 1, wherein said acetabular cup removal assembly further comprises a ball nose driver configured to move the adjustable curved blade from at least one first distance from said interchangeable head to at least one second distance from said interchangeable head.

3. The instrument of claim 1, wherein said position lock comprises a lock screw within a bore configured to secure said adjustable curved blade.

4. The instrument of claim 1, wherein said acetabular cup removal assembly further comprises a housing including a head adaptor to attach said interchangeable head and a blade adaptor to attach said adjustable curved blade.

5. The instrument of claim 1, wherein said elongated handle is modular.

6. The instrument of claim 1, wherein said adjustable curved blade is interchangeable so different blades can be used and/or is adjustable to accommodate different shell diameters using a ball nose driver.

7. The instrument of claim 1, wherein said interchangeable head has a size and said size can be adjusted based on the implant size.

8. The instrument of claim 1, further comprising a short handle adapted to be attached to said elongated handle to provide additional torque and rotation leverage to maneuver the adjustable curved blade.

9. An instrument for removal of an acetabular cup, the instrument comprising:
(a) an elongated handle; and
(b) an acetabular cup removal assembly attached to said elongated handle,
wherein said acetabular cup removal assembly includes:
(i) an interchangeable head for positioning and stabilizing the instrument within an acetabular liner or shell, (ii) an adjustable curved blade positioned to track around the outer diameter of the acetabular liner or shell to break the bone in-growth and/or cement, (iii) an adjustment mechanism configured to translate the adjustable curved blade perpendicular to the elongated handle, and (iv) a position lock configured to secure said adjustable curved blade at a selected distance from said interchangeable head.

10. The instrument of claim 9, wherein the adjustment mechanism is configured to be turned by is a ball nose driver.

11. The instrument of claim 9, wherein said adjustable curved blade is configured to translate from at least one first distance from said interchangeable head to at least one second distance from said interchangeable head.

12. The instrument of claim 9, wherein said adjustment mechanism comprises an adjustment screw configured to move the adjustable curved blade from at least one first distance from said interchangeable head to at least one second distance from said interchangeable head.

13. The instrument of claim 12, wherein said position lock comprises a lock screw within a bore configured to secure said adjustable curved blade.

14. The instrument of claim 9, wherein said position lock comprises a lock screw within a bore configured to secure said adjustable curved blade.

15. An instrument for removal of an acetabular cup, the instrument comprising:
(a) an elongated handle; and
(b) an acetabular cup removal assembly attached to said elongated handle, wherein said acetabular cup removal assembly includes:
(i) an interchangeable head for positioning and stabilizing the instrument within an acetabular liner or shell;
(ii) an adjustable curved blade positioned to track around the outer diameter of the acetabular liner or shell to break the bone in-growth and/or cement, wherein the adjustable curved blade comprises a distal end having a blade tip and a proximal end configured to insert into an opening in the acetabular cup removal assembly to connect the adjustable curved blade; and
(iii) a position lock configured to secure said adjustable curved blade at a selected distance from said interchangeable head.

16. The instrument of claim 15, wherein said acetabular cup removal assembly further comprises a housing comprising said opening to connect the adjustable curved blade to the acetabular cup removal assembly.

17. The instrument of claim 15, wherein said acetabular cup removal assembly further comprises an adjustment mechanism to translate the adjustable curved blade from at least one first distance from said interchangeable head to at least one second distance from said interchangeable head.

18. The instrument of claim 17, wherein said adjustment mechanism comprises an adjustment screw configured to move the adjustable curved blade.

19. The instrument of claim 15, wherein the elongated handle has a shaft axis and the adjustable curved blade is configured to translate perpendicular to the shaft axis to accommodate different acetabular liner or shell diameters.

20. The instrument of claim 15, wherein said position lock comprises a lock screw within a bore configured to secure said adjustable curved blade.

21. An instrument for removal of an acetabular cup, the instrument comprising:
(a) an elongated handle, and
(b) an acetabular cup removal assembly attached to said elongated handle,
wherein said acetabular cup removal assembly includes:
(i) an interchangeable head for positioning and stabilizing the instrument within an acetabular liner or shell, (ii) an adjustable curved blade positioned to track around the outer diameter of the acetabular liner or shell to break the bone in-growth and/or cement and configured to translate perpendicular to the elongated handle, and (iii) a position lock configured to secure said adjustable curved blade at a selected distance from said interchangeable head, wherein said position lock comprises a lock screw within a bore configured to secure said adjustable curved blade.

* * * * *